(12) United States Patent
Parihar et al.

(10) Patent No.: US 8,444,655 B2
(45) Date of Patent: May 21, 2013

(54) TISSUE RETRIEVAL DEVICE WITH MODULAR POUCH CARTRIDGE

(75) Inventors: Shailendra K. Parihar, Mason, OH (US); Sean P. Conlon, Loveland, OH (US); Kyle P. Moore, Mason, OH (US); Haresh D. Patil, Dhule (IN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 463 days.

(21) Appl. No.: 12/692,670

(22) Filed: Jan. 25, 2010

(65) Prior Publication Data

US 2011/0184430 A1 Jul. 28, 2011

(51) Int. Cl.
*A61B 17/22* (2006.01)
(52) U.S. Cl.
USPC .......................................................... 606/127
(58) Field of Classification Search
USPC ............... 606/110, 113, 114, 115, 127, 128, 606/184, 205, 206, 207, 208
See application file for complete search history.

(56) References Cited

U.S. PATENT DOCUMENTS

| 5,366,477 | A | * | 11/1994 | LeMarie et al. ............. 606/208 |
|---|---|---|---|---|
| 5,465,731 | A | | 11/1995 | Bell et al. |
| 5,480,404 | A | | 1/1996 | Kammerer et al. |
| 5,647,372 | A | | 7/1997 | Tovey et al. |
| 5,971,995 | A | | 10/1999 | Rousseau |
| 6,019,770 | A | | 2/2000 | Christoudias |
| 6,409,733 | B1 | | 6/2002 | Conlon et al. |
| 7,540,872 | B2 | * | 6/2009 | Schechter et al. ............. 606/50 |

FOREIGN PATENT DOCUMENTS

| DE | 10353006 WO | 6/2005 |
|---|---|---|
| WO | WO 2009/111717 | 9/2009 |

OTHER PUBLICATIONS

Merriam-Webster defnition of "cam" as obtained on Jul. 27, 2012; http://www.merriam-webster.com/dictionary/cam.*
International Search Report dated Jul. 13, 2011 for Application No. PCT/US2011/021038.
Abstract and English Machine Translation of German Application No. DE 10353006.

* cited by examiner

*Primary Examiner* — Ryan Severson
*Assistant Examiner* — Jonathan W Miles
(74) *Attorney, Agent, or Firm* — Frost Brown Todd LLC

(57) ABSTRACT

A specimen retrieval instrument comprises a handle assembly, an actuating rod, an introducer tube, and a retrieval bag. In some versions the specimen retrieval instrument further comprises a modular cartridge containing the retrieval bag. Upon translation of the actuating rod within the tube, the cartridge opens, releasing and opening the retrieval bag for receiving a specimen. A center spindle may be included where the spindle includes a slot for inserting a portion of the retrieval bag and wrapping the retrieval bag about the spindle. Some versions of the specimen retrieval instrument further comprise a rotating cam actuator that opens and closes a pair of support arms attached to the retrieval bag. Some versions of the specimen retrieval instrument further comprise rotating curved support arms operable to open and close the retrieval bag. Pins registered to helical grooves may provide rotation of the support arms as the support arms translate.

20 Claims, 21 Drawing Sheets

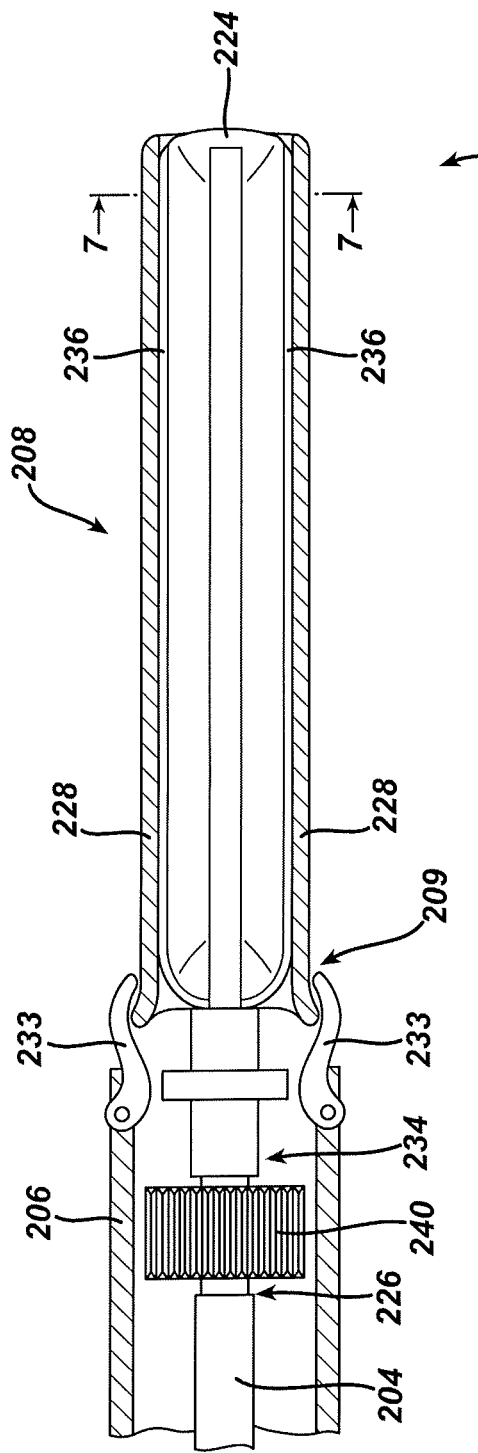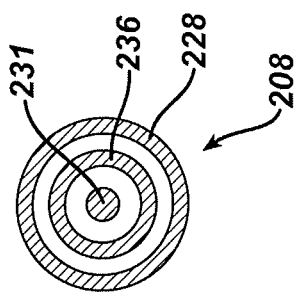

TISSUE RETRIEVAL DEVICE WITH MODULAR POUCH CARTRIDGE

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal cavity. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 6 is a top view of the distal end of another exemplary specimen retrieval instrument having a modular pouch cartridge with a center spindle and a pair of cartridge locks at the proximal end of the introducer tube, which is shown in cross section.

FIG. 7 is a cross section view taken along line 7-7 of FIG. 6, showing the outer shell, inner shell, and center spindle.

Figure 1:
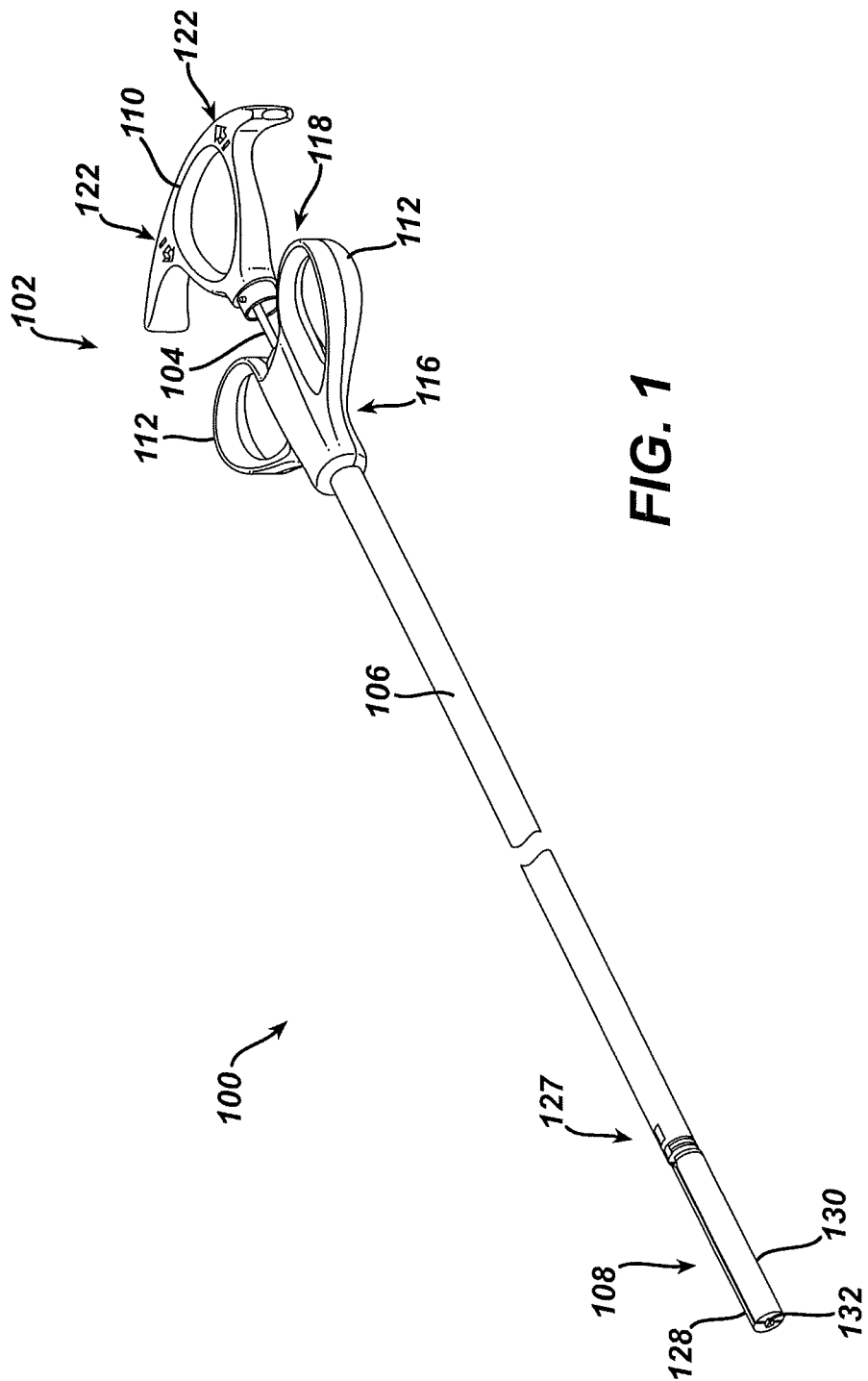
FIG. 1 is a perspective view of an exemplary specimen retrieval instrument having a modular pouch cartridge, with a retrieval bag in a closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a tissue retrieval device. It will be further appreciated that for convenience and clarity, spatial and directional terms such as "right," "left," "vertical," "horizontal," "upward," "downward," and the like, are used herein with respect to the drawings. However, surgical instruments are used in many orientations and positions, and these terms are not intended to be limiting or absolute in any way.

I. Modular Pouch Cartridge

A. Cartridge with Distal Latch and Distal Actuation

Referring to FIGS. 1-5, an exemplary specimen retrieval instrument 100 is shown. Specimen retrieval instrument 100 includes handle assembly 102, actuating rod 104, introducer tube 106, and cartridge 108. Each of these components will be discussed in greater detail below.

Figure 2:
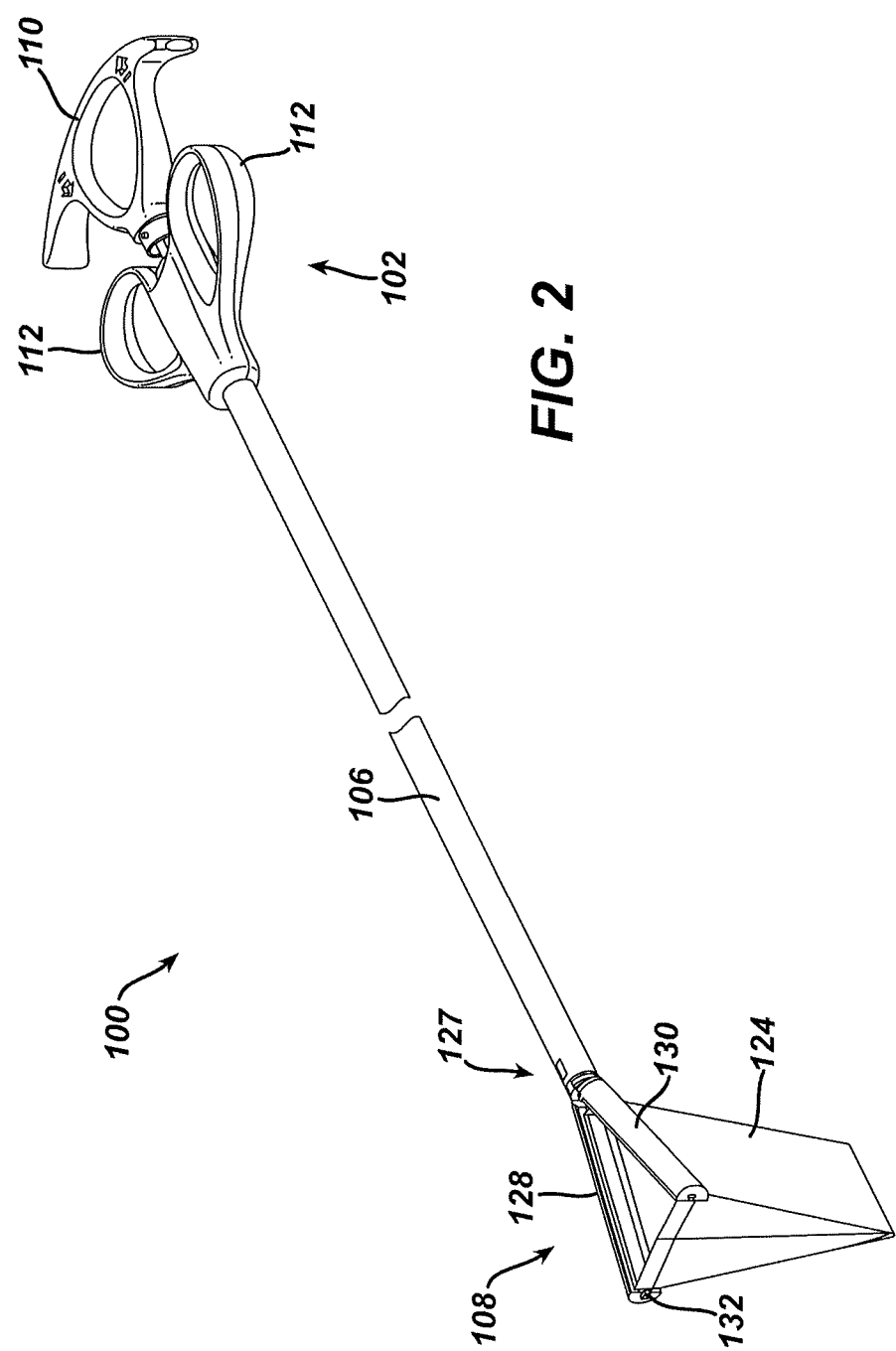
FIG. 2 is a perspective view of the specimen retrieval instrument of FIG. 1, with the retrieval bag in the open position.

Referring to FIGS. 1-3, handle assembly 102 includes thumb ring 110, finger rings 112, and an internal passageway (not shown). The internal passageway extends from distal end 116 of finger rings 112 to proximal end 118 of finger rings 112. Actuating rod 104 extends slidably through passageway, connecting to thumb ring 110 at the proximal end of actuating rod 104. Finger rings 112 are connected to introducer tube 106. Thumb ring 110 is moveable relative to finger rings 112 and introducer tube 106, and actuating rod 104 moves in unison with thumb ring 110. Additional optional features of handle assembly 102 may include markings 122 to indicate directional movement of thumb ring 110 as well as markings (not shown) to indicate the orientation of retrieval bag 124 initially held within cartridge 108—e.g. a marking indicating "this end up" such that the opening of retrieval bag 124 is properly located during use.

Referring to FIG. 1, specimen retrieval instrument 100 is shown in an initial position. In this initial position, thumb ring 110 of handle assembly 102, and therefore actuating rod 104, are retracted proximally to some extent. Cartridge 108 is secured to the distal end of introducer tube 106. Cartridge 108 is also operably coupled with the distal end 126 of actuating rod 104, as will be described in greater detail below. When actuating rod 104 is in the initial, proximal position, cartridge 108 is in a closed position, with first portion 128 and second portion 130 of cartridge 108 immediately adjacent one another and held in place by latch 132. Cartridge 108 of the present example is sized such that its outer diameter is approximately the same size as the outer diameter of introducer tube 106 when cartridge 108 is in the closed position shown in FIG. 1. In addition, the interface between cartridge 108 and introducer tube 106 is such that their outer surfaces provide a substantially smooth transition from cartridge 108 to introducer tube 106. The outer diameters of cartridge 108 and introducer tube 106 are sized such that they may be introduced to a surgical site through a trocar or other type of device. By way of example only, the outer diameters of cartridge 108 and introducer tube 106 may be between approximately 5 mm (inclusive) and approximately 15 mm (inclusive) (e.g., approximately 10 mm, etc.). Alternatively, these components may have any other suitable dimensions.

Alternatively, cartridge 108 and/or introducer tube 106 may have any other suitable outer diameters. In some versions, the outer diameter of cartridge 108 is slightly smaller than the outer diameter of introducer tube 106. For instance, in some such versions, the outer diameter of cartridge 108 is even smaller than then inner diameter of introducer tube 106, such that cartridge 108 may be retracted proximally within introducer tube 106. Thus, in such versions, cartridge 108 may be retracted within introducer tube 106 as introducer tube 106 is being introduced to a surgical site (e.g., inserted through a trocar, etc.); and then cartridge 108 may be advanced distally (e.g., by pushing thumb ring 110 distally relative to finger rings 112, etc.) to extend from the distal end of introducer tube 106 to reach the position shown in FIG. 1 once introducer tube 106 has sufficiently reached the surgical site.

Referring to FIG. 2, specimen retrieval instrument 100 is shown in an open position. In the open position, thumb ring 110 of handle assembly 102, and therefore actuating rod 104, are extended distally from the initial position described above. Cartridge 108 is open, exposing retrieval bag 124. More specifically, latch 132 is no longer holding first portion 128 and second portion 130 of cartridge 108 closed, and instead first and second portions 128, 130 are angled open in a triangular orientation such that retrieval bag 124 may open. In some versions, distal positioning of thumb ring 110 relative to finger rings 112 is sufficient to decouple latch 132 to allow portions 128, 130 of cartridge 108 to reach the open configuration shown in FIG. 2. In some other versions, a separate instrument (e.g., conventional surgical grasper, etc.) is used to decouple latch 132. Having set forth the general configuration of the initial and open positions of specimen retrieval instrument 100, additional detail of exemplary component configurations and operability will be discussed below.

Figure 3A:
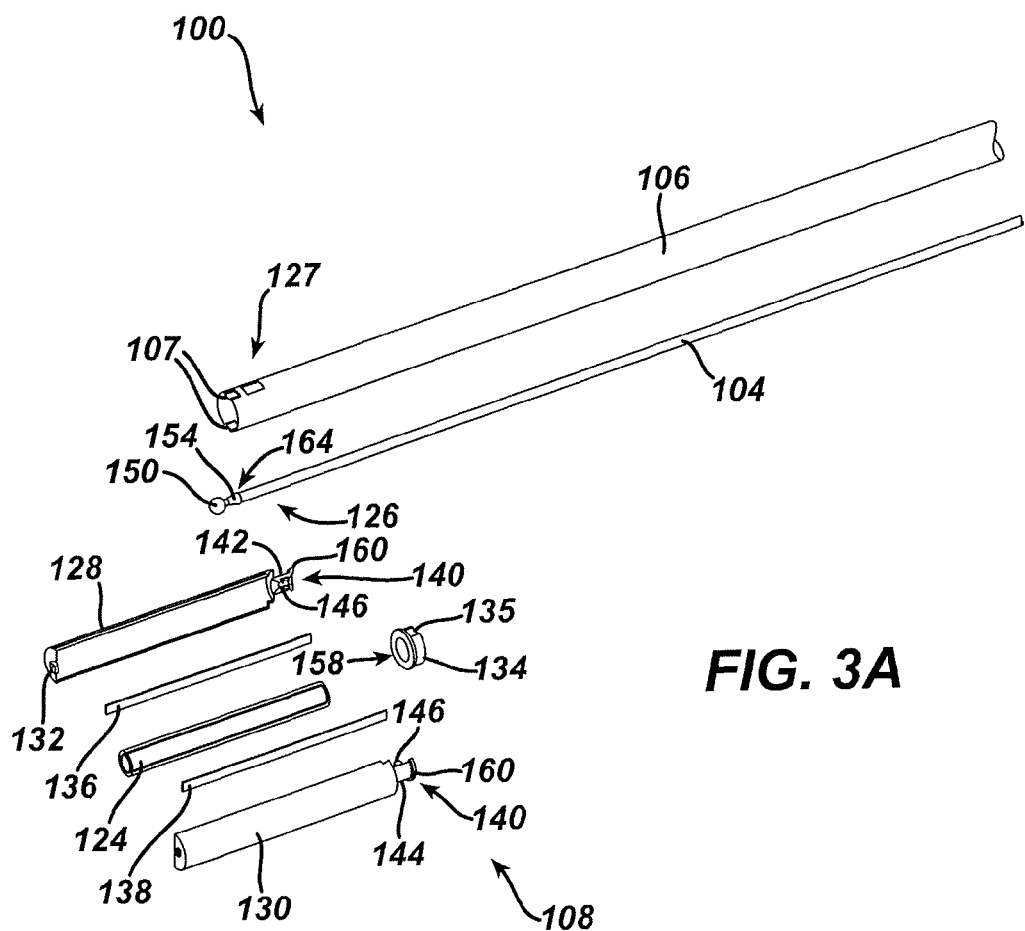
FIG. 3A is a partial exploded view of the specimen retrieval instrument of FIG. 1, showing components of the distal portion of the specimen retrieval instrument.
Figure 3B:
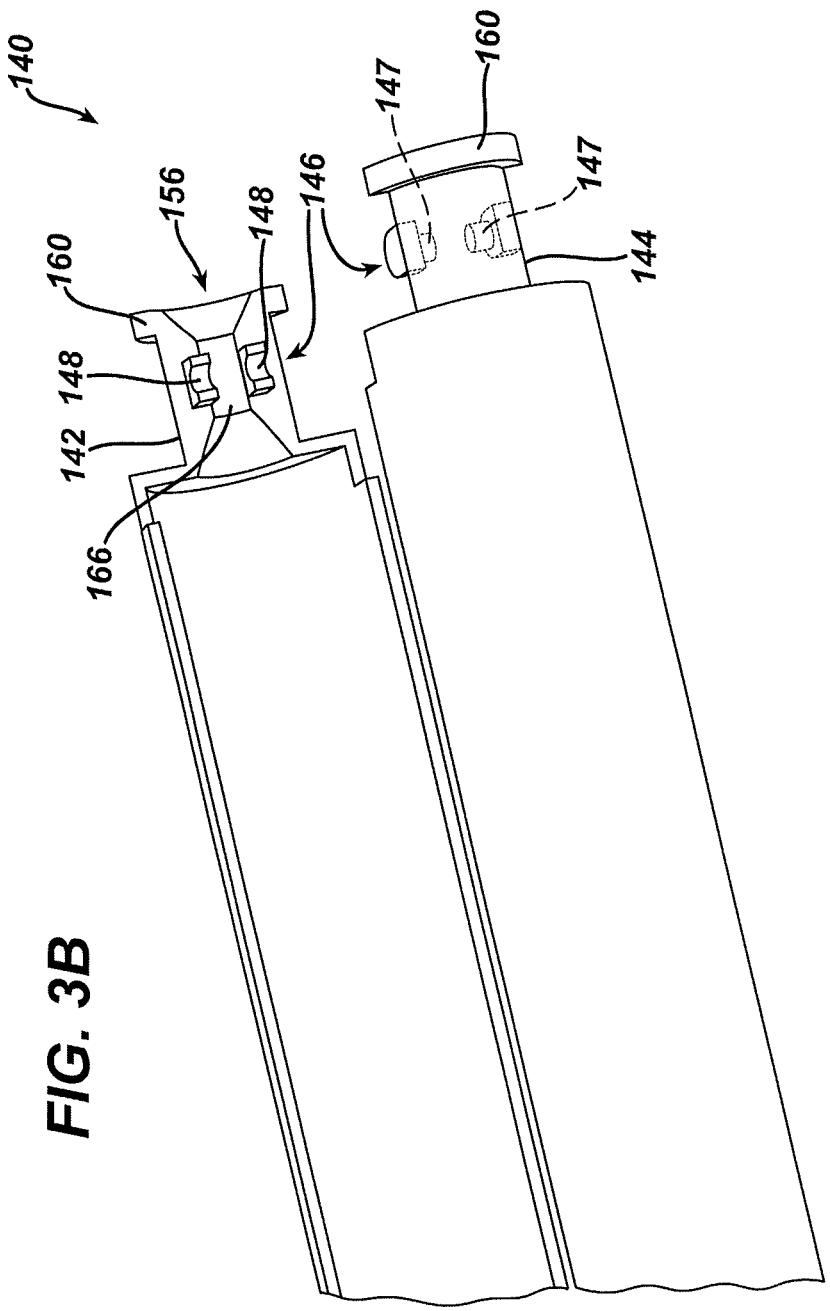
FIG. 3B is a partial perspective view of collar components of the specimen retrieval instrument of FIG. 1.
Figure 4:
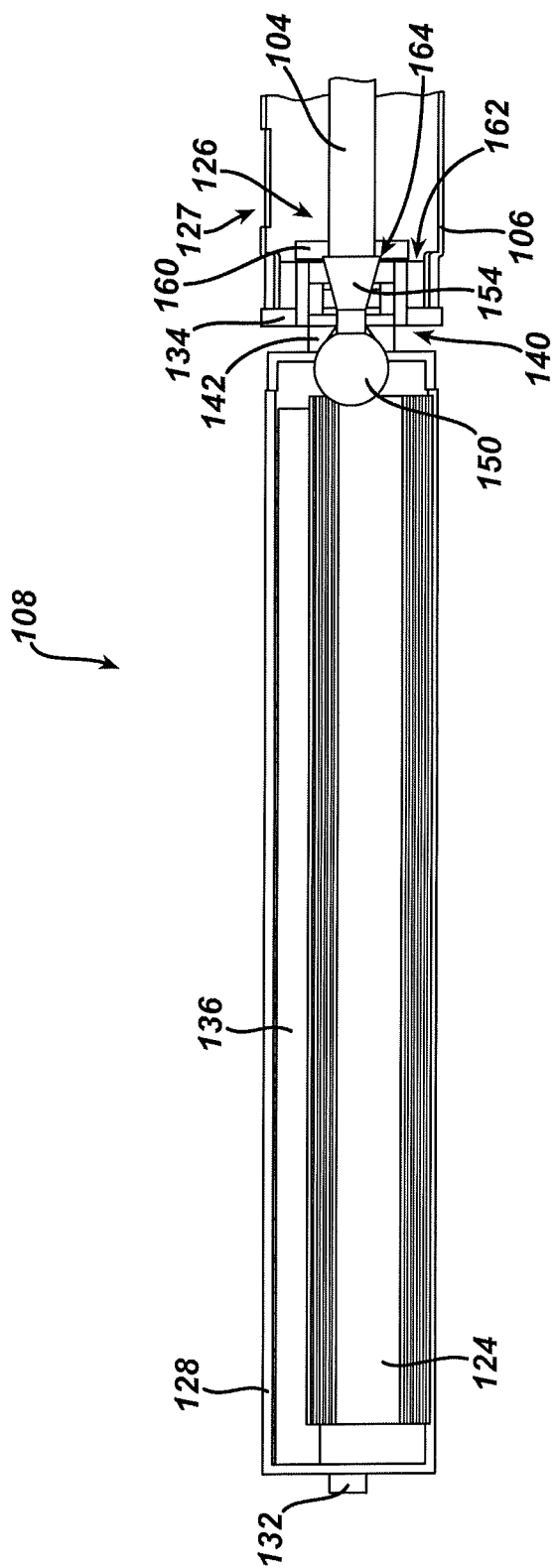
FIG. 4 is a side view in cross section of the distal end of the specimen retrieval instrument of FIG. 1.
Figure 5:
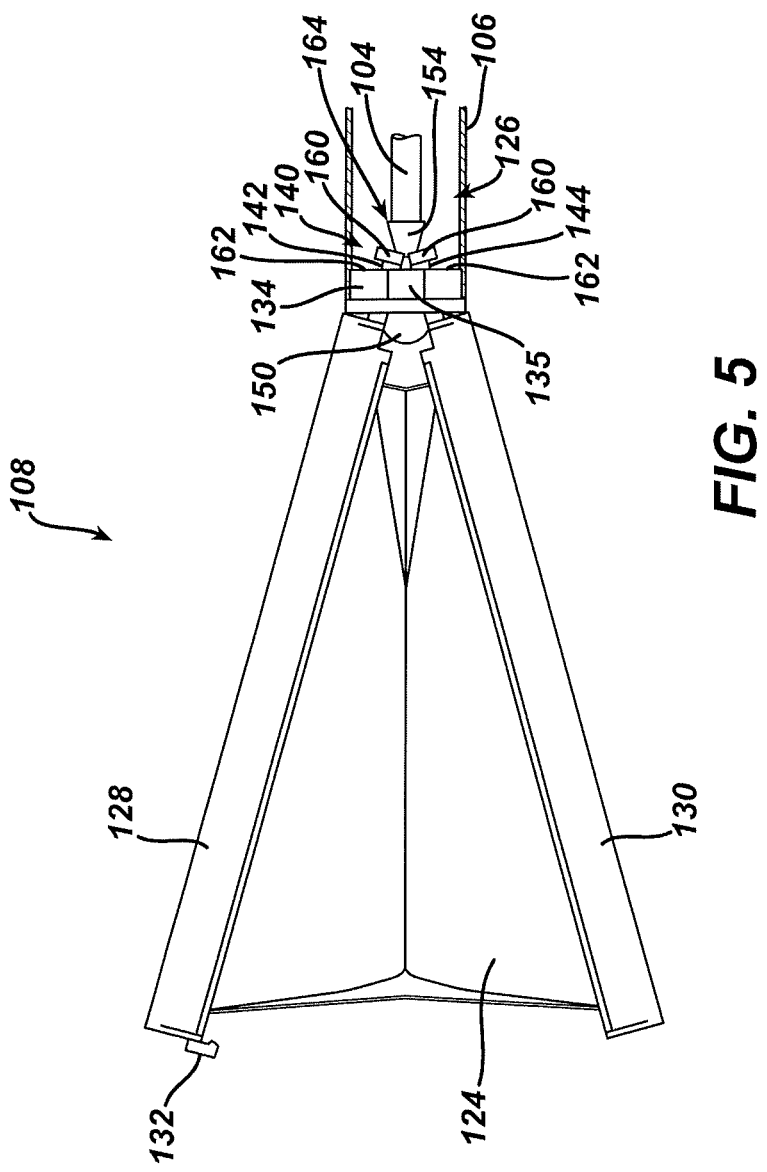
FIG. 5 is a top view of the distal end of the specimen retrieval instrument of FIG. 1, with the retrieval bag in the open position and with the introducer tube in cross section.

Referring to FIGS. 3A, 3B, and 4, a more detailed view of the distal portion of specimen retrieval instrument 100 is shown. As seen in FIGS. 3A-3B, cartridge 108 of the present example comprises first portion 128, second portion 130, retrieval bag 124, adapter 134, first support arm 136, and second support arm 138. Retrieval bag 124 is shown in a rolled-up configuration in FIG. 3A. Support arms 136, 138 are associated with opposing upper sides of retrieval bag 124 such that when support arms 136, 138 are spread apart, retrieval bag 124 will open. For instance, support arms 136, 138 may be inserted through corresponding slots or pockets (not shown) or other features adjacent to a top opening defined by retrieval bag 124. Furthermore, first support arm 136 is associated with first portion 128 of cartridge 108, while second support arm 138 is associated with second portion 130 of cartridge 108. As will be described in further detail below, the association between first and second support arms 136, 138 with respective first and second portions 128, 130 of cartridge 108 allow for support arms 136, 138 to spread apart and open retrieval bag 124 upon first and second portions 128, 130 of cartridge 108 spreading apart.

Still referring to FIGS. 3A, 3B, and 4, first and second portions 128, 130 of cartridge 108 together define a proximal collar 140. Collar 140 is split with a first portion 142 of collar 140 located on first portion 128 of cartridge 108, and a second portion 144 of collar 140 located on second portion 130 of cartridge 108. First and second portions 142, 144 of collar 140 may be fit together with connection 146, allowing first and second portions 128, 130 of cartridge 108 to pivot about connection 146. For example, connection 146 may include a pair of pins 147 and a pair of clips 148 configured to receive the pair of pins 147. Of course other suitable connection types will be appreciated by those of ordinary skill in the art based upon the teachings herein.

Again referring to FIGS. 3A and 4, actuating rod 104 includes sphere 150 at its distal end 126. Furthermore, sphere 150 is connected to actuating rod 104 by conical member 154. Collar 140 of cartridge defines a recess 156 that has a shape similar to an hourglass resting upon its side as shown in FIG. 3B. As shown in FIG. 4, sphere 150 and conical member 154 are configured to fit within recess 156, with sphere 150 positioned within the distal portion of recess 156, and conical member 154 positioned within the proximal portion of recess 156. With actuating rod 104 and collar 140 of cartridge 108 so positioned, adapter 134 of cartridge 108 is configured to fit over collar 140. In particular, adapter 134 of the present example defines an opening 158. Opening 158 is sized such that adapter 134 fits around collar 140 but with lip 160 of collar 140 adjacent proximal surface 162 of adapter 134. Adapter 134 also includes diametrically opposed recesses 135, which are configured to engage complementary diametrically opposed indentations formed in the distal end of introducer tube 106. With this configuration, the proximal end of cartridge 108 is securely held in place, but with cartridge 108 able to rotate about connection 146 as discussed in greater detail below.

In use, specimen retrieval instrument 100 may initially have the arrangement shown in FIGS. 1 and 4, where thumb ring 110 and actuating rod 104 are retracted proximally. In this arrangement, the distal portion of specimen retrieval instrument 100 may be inserted within a patient through a suitable incision opening or access port created by a trocar or some other device. Once positioned within the patient, thumb ring 110 may be pulled proximally away from finger rings 112. This action drives actuating rod 104 proximally, causing sphere 150 and conical member 154 to move proximally as well. As actuating rod 104 is pulled proximally, sphere 150 pushes against interior wall 166 of collar 140 defining the hourglass shaped recess 156. As sphere 150 moves proximally and pushes against interior wall 166, force is exerted upon first and second portions 128, 130 of cartridge 108 such that first and second portions 128, 130 pivot about connection 146, moving outward from a longitudinal axis of cartridge 108. Support arms 136, 138 are thereby spread apart, which opens the top opening of retrieval bag 124. The spreading of support arms 136, 138 and/or the material properties of retrieval bag 124 may suffice to unfurl retrieval bag 124 from the rolled-up position shown in FIG. 3A to the unrolled and opened position shown in FIG. 2. In addition or in the alternative, some other instrument (e.g., conventional surgical grasper, etc.) may be used to assist in unfurling/unrolling of retrieval bag 124 once portions 128, 130 and support arms 136, 138 have been spread open.

In the present example, support arms 136, 138 each comprise a single unitary piece of material without joints or breaks. However, in some other versions, one or more of support arms 136, 138 may comprise a segmented construction. In some such versions, one or more of support arms 136, 138 may comprise a single piece of material incorporating one or more hinges or flex points, including but not limited to living hinges, configured to allow that particular support arm 136, 138 to transition between the storage configuration and the desired expanded configuration. In some other versions, one or more of support arms 136, 138 may comprise at least two separate components hinged or connected together to allow that particular support arm 136, 138 to transition between the storage configuration and the desired expanded configuration. Still other suitable alternative configurations for support arms 136, 138 will be apparent to those of ordinary skill in the art in view of the teachings herein.

In some versions where latch 132 is present, before first and second portions 128, 130 will pivot about connection 146, latch 132 must be disengaged. One manner of disengaging latch 132 may involve the force upon first and second portions 128, 130 created by distal actuation of actuating rod 104 being sufficient to overcome a resilient bias of latch 132 to remain in an engaged position. In such an example, when the force reaches a certain degree, the resilient bias of latch 132 to remain in an engaged position is overcome and latch 132 will disengage. Upon disengagement of latch 132, first and second portions 128, 130 may move outward from a longitudinal axis defined by cartridge 108. Of course, engagement and disengagement of latch 132 may be accomplished in a number of other ways. For instance, latch 132 may be engaged or disengaged by using another instrument, such as a grasper. Various other suitable ways in which latch 132 may be engaged and/or disengaged will be apparent to those of ordinary skill in the art in view of the teachings herein. Once latch 132 has been disengaged in the present example, the proximal movement of actuating rod 104 opens cartridge 108 as described above and allows retrieval bag 124 to open under the force of gravity or with some other assistance, e.g. being pulled opened by another instrument such as a grasper. Once retrieval bag 124 has been opened, specimen retrieval instrument 100 may have the arrangement shown in FIGS. 2 and 5.

Once a specimen has been placed within retrieval bag 124, thumb ring 110 may be advanced distally toward finger rings 112 to close cartridge 108 and retrieval bag 124. Closure of retrieval bag 124 may be accomplished by applying a distal force to collar 140. This distal force may be created by distal movement of actuating rod 104 and the interaction of conical member 154 of actuating rod 104 with interior wall 166 of hourglass shaped recess 156. More specifically, the shape of conical member 154 is such that at its proximal end 164 conical member 154 has the greatest width. As thumb ring 110 is pushed distally, this distal movement drives actuating rod 104 and conical member 154 distally. Proximal end 164 of conical member 154 pushes against interior wall 166 of collar 140 defining the hourglass shaped recess 156. In particular, distally urged conical member 154 pushes against interior wall 166, and a force is exerted upon collar 140 such that first and second portions 128, 130 of cartridge 108 pivot about connection 146, moving inward toward the longitudinal axis defined by cartridge 108. In some versions where latch 132 is present, when first and second portions 128, 130 of cartridge 108 are sufficiently close to one another, latch 132 engages. In the present example, the distal movement of actuating rod 104 causes cartridge 108 and retrieval bag 124 to close as described above in preparation for removal of specimen retrieval instrument 100, including retrieval bag 124 and a specimen contained therein, from the patient.

Specimen retrieval instrument 100 may permit various modes for removing retrieval bag 124 once a specimen is captured. For instance, in some versions retrieval bag 124 and/or cartridge 108 may be removed from the patient along with the other components of specimen retrieval instrument 100. In other words, retrieval bag 124, cartridge 108, and introducer tube 106 may be unitarily removed from the patient substantially contemporaneously.

In some other versions, specimen retrieval instrument 100 is configured such that retrieval bag 124 and/or cartridge 108 may be removed from specimen retrieval instrument 100 while retrieval bag 124 and/or cartridge 108 are within the patient. Some such versions facilitate removal of retrieval bag 124 and/or cartridge 108 separate from removal of the other components of specimen retrieval instrument 100. In some versions, this may be accomplished by, among other ways, retrieval bag 124 being removable from first and second support arms 136, 138. For instance, in some versions specimen retrieval instrument 100 may include a closure string connected to retrieval bag 124 and having a slipknot attachment to actuating rod 104. Pulling the slipknot loose and retracting the actuating rod 104 may permit detachment of retrieval bag 124 and the closure string from the other components of specimen retrieval instrument 100. In some such versions, a user may pull the closure string to close retrieval bag 124. By way of example only, such a closure mechanism may be configured in accordance with the teachings of U.S. Pat. No. 6,409,733, entitled "Specimen Retrieval Bag," issued Jun. 25, 2002, which is incorporated herein by reference. Still in other versions, it may be feasible to incorporate a closure string with cartridge 108 and retrieval bag 124; and to eject cartridge 108 and retrieval bag 124 from specimen retrieval instrument 100 such that cartridge 108 and retrieval bag 124 may be removed from the patient separate from other components of specimen retrieval instrument 100.

As yet another variation that includes a closure string about retrieval bag 124, cartridge 108 may include cutting/shearing features that sever retrieval bag 124 from support arms 136, 138 when portions 128, 130 are moved from the open configuration to the closed configuration, such that retrieval bag 124 is separated from cartridge 108 when portions 128, 130 are moved from the open configuration to the closed configuration. In some such versions, a closure string may be positioned below the region at which retrieval bag 124 is cut, allowing retrieval bag 124 to remain closed by the closure string after retrieval bag 124 is severed from arms 136, 138 and allowing the closure string to remain uncut after retrieval bag 124 is severed from arms 136, 138. Still other suitable ways in which cartridge 108 and/or retrieval bag 124 may be removed from a patient will be apparent to those of ordinary skill in the art in view of the teachings herein.

While the above description provides adequate disclosure to enable one of ordinary skill in the art to make and use specimen retrieval instrument 100, based on the teachings herein, those of ordinary skill in the art will appreciate that various modifications may provide additional features or functionality. For example, it will be appreciated that cartridge 108 may be modified to incorporate a specific bias designed to maintain cartridge 108 in a desired open or closed position. For instance, where cartridge 108 is modified to be biased to an open position, once opened, a user would not necessarily need to hold thumb ring 110 in the distal position to maintain an open configuration of retrieval bag 124. Of course, a user may not necessarily need to hold thumb ring 110 in the distal position to maintain an open configuration of retrieval bag 124 if such a bias were omitted. For instance, specimen retrieval instrument 100 may include a latching or ratcheting mechanism that is configured to hold thumb ring 110 in the distal position. Such a mechanism may be selectively releasable to allow thumb ring 110 to be retracted from the distal position to the proximal position.

As another merely illustrative variation, cartridge 108 could be modified to be biased to a closed position. In some versions of this variation, a user would need to hold thumb ring 110 in the distal position to maintain retrieval bag 124 open to capture a specimen, but once the specimen is captured, releasing thumb ring 110 allows cartridge 108 and retrieval bag 124 to close. In some other versions of this variation, specimen retrieval instrument 100 may include a latching or ratcheting mechanism that is configured to hold thumb ring 110 in the distal position. Again, such a mechanism may be selectively releasable to allow thumb ring 110 to be retracted from the distal position to the proximal position. Also, in addition or instead of imparting bias to cartridge 108, such bias may be imparted to other components, such as actuating rod 104 and thumb ring 110, to achieve similar operability.

In some versions, modifications may include actuating rod 104 comprising features operable with features of introducer tube 106 or other components to prevent inadvertent extension of actuating rod 104 and premature opening of cartridge 108 and retrieval bag 124. For example, actuating rod 104 may include a lock or stop (e.g., similar to a "safety mechanism") that may be released once a user is ready to open cartridge 108 and retrieval bag 124. Other suitable ways in which specimen retrieval instrument 100 may be configured to prevent inadvertent extension of actuating rod 104 and premature opening of cartridge 108 and retrieval bag 124 will be apparent to those of ordinary skill in the art in view of the teachings herein.

In some versions, cartridge 108 may be available in various sizes having various sized retrieval bags 124. A surgeon may thus select a particular cartridge 108 from a supply of various cartridges 108 having differently sized retrieval bags 124, to select a retrieval bag 124 that is most appropriate or otherwise desired for a particular procedure or setting. In such versions, the desired sized cartridge 108 and retrieval bag 124 may be attached to actuating rod 104 prior to insertion of specimen retrieval instrument 100 within a patient. Various suitable ways in which cartridge 108 may be removably coupled with specimen retrieval instrument to provide such modularity will be apparent to those of ordinary skill in the art in view of the teachings herein. Still various other suitable features, components, configurations, and operabilities that may be incorporated into specimen retrieval instrument 100 will be apparent to those of ordinary skill in the art in view of the teachings herein.

B. Cartridge with Proximal Lock and Retractable Center Spindle

Referring now to FIGS. 6-9, the distal portion 201 of another exemplary specimen retrieval instrument is shown. The specimen retrieval instrument of FIGS. 6-9 may include handle assembly (not shown), actuating rod 204, introducer tube 206, and cartridge 208. These components will be discussed in greater detail below. While the handle assembly of this exemplary specimen retrieval instrument is not shown in FIGS. 6-9, various suitable components, features, and configurations that the handle assembly may have will be apparent to those of ordinary skill in the art in view of the teachings herein. By way of example only, the handle assembly may have a configuration that is substantially identical to the configuration of handle assembly 102 described above.

Figure 8:
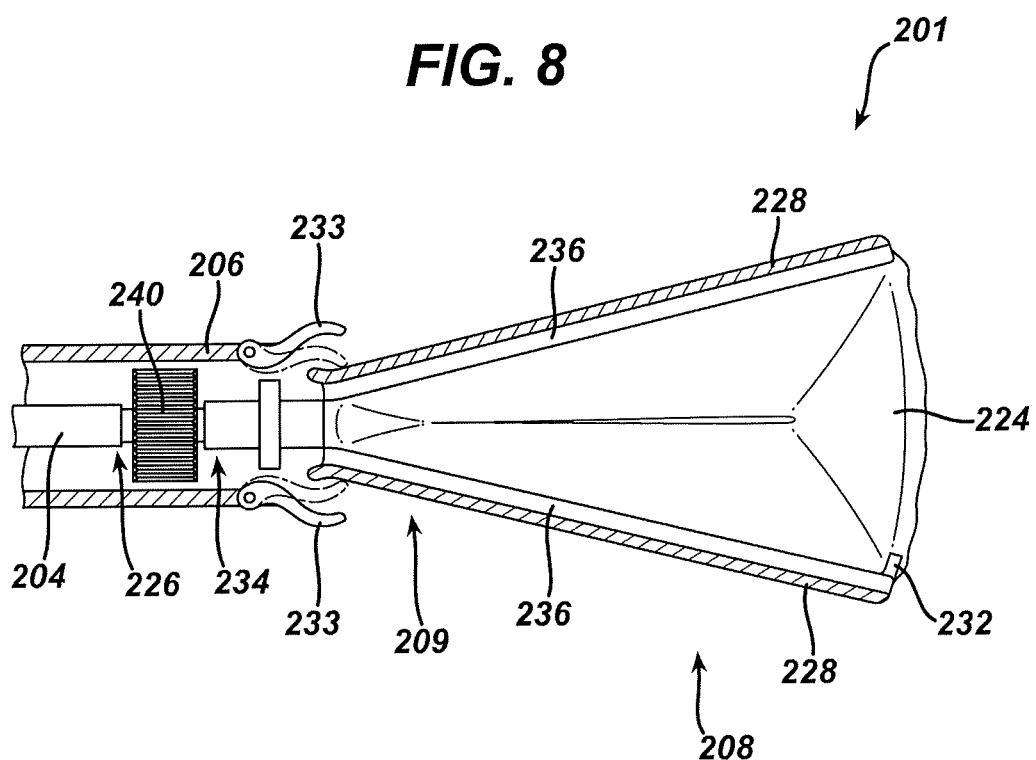
FIG. 8 is a top view of the distal end of the specimen retrieval instrument of FIG. 6, with the retrieval bag in the open position and with the center spindle retracted from view, with the introducer tube shown in cross section.
Figure 9:
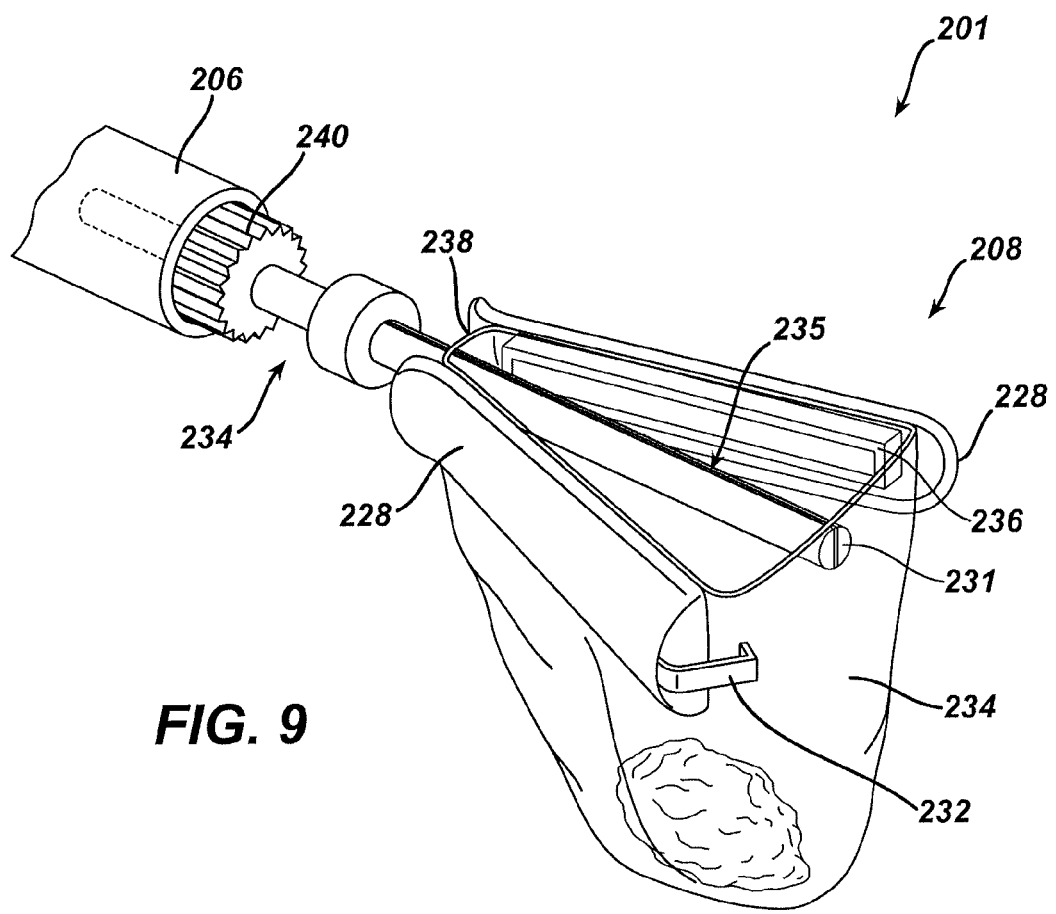
FIG. 9 is a perspective view of the distal end of the specimen retrieval instrument of FIG. 6, with the retrieval bag in the open position, prior to retraction of the center spindle.

Referring to FIGS. 6 and 7, distal portion 201 of the specimen retrieval instrument is shown in an initial position. In the initial position, actuating rod 204 is extended distally and cartridge 208 is in a closed position and connected to the distal end 226 of actuating rod 204. Referring to FIGS. 8 and 9, distal portion 201 of the specimen retrieval instrument is shown in an open position. In the open position, cartridge 208 is open to expose retrieval bag 224.

As shown in FIGS. 6-9, cartridge 208 of the present example includes an outer shell 228, an inner shell 236, a center spindle 231, a distal latch 232, a proximal lock 233, a retrieval bag 224, and an adapter 234. Furthermore, outer shell 228 and inner shell 236 may each be split into two halves, such that outer shell 228 and inner shell 236 may pivot from closed to open positions as shown in FIGS. 6, 8, and 9. In some versions distal latch 232 and/or proximal lock 233 may be omitted. In some versions, center spindle 231 may be included with actuating rod 204 instead of being included with cartridge 208, while in some versions center spindle 231 may be omitted entirely. Still in some versions inner shell 236 may be replaced by spring arms or some other component suited to attach to retrieval bag 224.

In some versions having center spindle 231, center spindle 231 may include slot 235. Slot 235 may be configured to hold a portion of retrieval bag 224 such that rotating center spindle 231 about the axis defined by spindle 231 in a first direction causes retrieval bag 224 to wrap about center spindle 231, such as for storing retrieval bag 224 before it is fully deployed and opened for receipt of a specimen. In some such versions, rotating center spindle 231 about the axis defined by spindle 231 in a second direction causes retrieval bag 224 to unwrap from center spindle 231, such as for deploying retrieval bag 224. By way of example only, the top portion of bag 224 (e.g., the portion of bag 224 defining the opening of bag 224) may be secured to one or both shells 228, 236; while the bottom portion of bag 224 may be disposed in the slot 235 of spindle 231 for wrapping bag 224 about spindle 231.

Rotation of spindle 231 relative to other components of the tissue retrieval device may be effected through gear 240. For instance, gear 240 may be rotationally coupled with spindle 231 such that gear 240 and spindle 231 rotate concomitantly. Gear 240 may be in communication with another gear (not shown) that is coupled with a shaft (not shown) that extends proximally through introducer tube 206. Such a shaft may extend substantially parallel to actuating rod 204 and may be coupled with a knob or other device that is operable to rotate the shaft (and, therefore, rotate gear 240 and spindle 231). Such a knob may be part of the handle assembly of the tissue retrieval device. To the extent that spindle 231 is retractable, the engagement between spindle 231 and gear 240 may permit spindle 231 to slide relative to gear 240 while also allowing gear 240 to rotate spindle 231. For instance, spindle 231 and gear 240 may be engaged with key-keyway configuration, mating hex features, etc.

As another merely illustrative example, spindle 231 and actuating rod 204 may be substantially unitary, such that actuating rod 204 may be rotated in order to rotate spindle 231. In some such versions, shells 228, 236 and introducer tube 206 may be rotationally grounded relative to actuating rod 204 and spindle 231, such that shells 228, 236 and introducer tube 206 remain substantially stationary as actuating rod 204 and spindle 231 rotate. Various suitable structures and configurations for providing such operability will be apparent to those of ordinary skill in the art in view of the teachings herein.

In some versions having center spindle 231, center spindle 231 may be retractable within either actuating rod 204 or introducer tube 206. In such versions, once retrieval bag 224 has been deployed and opened, center spindle 231 may be retracted to provide an unobstructed opening in retrieval bag 224 for receipt of a specimen. In such versions where center spindle 231 is retractable, such retraction may be accomplished by proximal movement of the thumb ring of the handle assembly. Center spindle 231 may thus be slidably disposed within actuating rod 204, such that center spindle translates proximally within actuating rod 204. Alternatively, any other suitable configurations may be used.

In some versions having center spindle 231 and distal latch 232, center spindle 231 may be extended distally such that center spindle 231 may contact distal latch to cause distal latch to disengage, thus permitting cartridge 208 to open. As another variation of such versions, the distal end of outer shell 228 may be deformable, such that distal advancement of spindle 231 against the interior of distal end of outer shell 228 causes deformation of outer shell 228, which in turn causes distal latch 232 to disengage. In other versions without center spindle 231, or where center spindle 231 may not be extended, distal latch 232 may be opened with the assistance of another instrument. For example, a grasper may be used to force distal latch 232 to disengage. Alternatively, any other suitable configurations or techniques may be used to disengage distal latch 232. Of course, distal latch 232 may even be omitted if desired.

Proximal lock 233 may be used to selectively couple cartridge 208 with introducer tube 206. For instance, arms of proximal lock 233 may be rotated forward to substantially secure cartridge 208 with introducer tube 206; while arms of proximal lock 233 may be rotated rearward to release cartridge 208 from introducer tube 206. In versions where proximal lock 233 is present, proximal lock 233 may be disengaged from cartridge 208 by either an actuation mechanism associated with the handle assembly (e.g., a push/pull cable or rod, etc.) or some other component of the specimen retrieval instrument; or by assistance from another instrument, e.g. a grasper. Proximal lock 233 may also be resiliently biased to position its arms to engage cartridge 208. In some versions, proximal lock 233 does not interfere with or otherwise impact opening and closing of cartridge 208. In some other versions, proximal lock 233 is operable to assist in opening and/or closing of cartridge 208. By way of example only, proximal lock 233 may be operable to selectively lock cartridge 208 in the closed position, thereby complementing distal lock 232. Such optional roles in the opening and/or closing of cartridge 208 that proximal lock 233 may be assumed by proximal lock 233 in addition to or in lieu of its role in selectively securing cartridge 208 to introducer tube 206. Furthermore, while proximal lock 233 comprises pivoting arms in the present example, proximal lock 233 may alternatively take a variety of other forms. Of course, proximal lock 233 may even be omitted if desired.

In use, the specimen retrieval instrument may initially have the arrangement shown in FIGS. 6 and 7. In this arrangement, the distal portion 201 of the specimen retrieval instrument may be inserted within a patient through a suitable incision opening or access port created by a trocar or some other component. Once positioned within the patient, distal latch 232 may be disengaged as discussed above to permit cartridge 208 to open.

Cartridge 208 may be biased to an open position such that when other structures are not inhibiting cartridge 208, cartridge 208 will seek an open position. In some versions inner shell 236 may be secured to retrieval bag 224 and also to outer shell 228. Furthermore, inner shell 236 may include one or more spring members 238 that provide the halves of inner shell 236 with the open bias. Since outer shell 228 encompasses inner shell 236, the open bias of inner shell 236 may be sufficient to bias outer shell 228 open without other biasing structures dedicated solely to outer shell 228. Of course outer shell 228 may be configured or modified to contain dedicated biasing structures of its own. The bias provided by spring members 238 in the present example is sufficient to cause the two opposing halves of each shell 236, 238 to separate as soon as distal latch 232 is decoupled, thereby opening bag 224.

With cartridge 208 open, retrieval bag 224 may unfurl under the force of gravity or with assistance from some other instrument, e.g. a grasper. Where center spindle 231 is present, center spindle 231 may be rotated about its longitudinal axis, e.g. by rotating actuating rod 208 by rotating the thumb ring of the handle assembly, to unwrap retrieval bag 224. Alternatively, a knob or other feature that communicates with gear 240 via a shaft and other gear may be rotated to rotate center spindle 231. When retrieval bag 224 is sufficiently unwrapped, the weight of retrieval bag 224 will cause any portion of retrieval bag 224 held by slot 235 to be released. Alternatively, any portion of retrieval bag 224 held by slot 235 may be released with the assistance of another instrument, e.g. a grasper. Once retrieval bag 224 has been opened and unfurled, the specimen retrieval instrument may have the arrangement shown in FIGS. 8 and 9.

Once a specimen has been placed within retrieval bag 224, the thumb ring of the handle assembly may be retracted to actuate closure of cartridge 208 and retrieval bag 224. In some versions, closure of cartridge 208 and retrieval bag 224 may be accomplished by retracting the proximal end 209 of cartridge 208 within distal end 227 of introducer tube 206. In some versions, closure of cartridge 208 may be accomplished by assistance from another instrument. For example, a grasper may contact outer shell 228 and force cartridge 208 to a closed position. Further, grasper may engage distal latch 232 to retain cartridge 208 in closed position. With retrieval bag 224 closed, the specimen retrieval instrument, including retrieval bag 224 and specimen, may be removed from the patient.

The specimen retrieval instrument of the present example may permit various modes for removing retrieval bag 224 once a specimen is captured. For instance, in some versions retrieval bag 224 and/or cartridge 208 may be removed from the patient along with the other components of the specimen retrieval instrument. In other words, retrieval bag 224, cartridge 208, and introducer tube 206 may be unitarily removed from the patient substantially contemporaneously.

In some other versions, the specimen retrieval instrument is configured such that retrieval bag 224 and/or cartridge 208 may be removed from the specimen retrieval instrument while retrieval bag 224 and/or cartridge 208 are within the patient. Some such versions facilitate removal of retrieval bag 224 and/or cartridge 208 separate from removal of the other components of the specimen retrieval instrument. In some versions, this may be accomplished by, among other ways, retrieval bag 224 being removable from shells 228, 236. For instance, in some versions the specimen retrieval instrument may include a closure string connected to retrieval bag 224 and having a slipknot attachment to actuating rod 204. Pulling the slipknot loose and retracting the actuating rod 204 may permit detachment of retrieval bag 224 and the closure string from the other components of the specimen retrieval instrument. In some such versions, a user may pull the closure string to close retrieval bag 224. By way of example only, such a closure mechanism may be configured in accordance with the teachings of U.S. Pat. No. 6,409,733, entitled "Specimen Retrieval Bag," issued Jun. 25, 2002, which is incorporated herein by reference. Still in other versions, it may be feasible to incorporate a closure string with cartridge 208 and retrieval bag 224; and to eject cartridge 208 and retrieval bag 224 from the specimen retrieval instrument such that cartridge 208 and retrieval bag 224 may be removed from patient separate from other components of the specimen retrieval instrument. Proximal lock 233 may be actuated to provide or otherwise facilitate such ejection.

As yet another variation that includes a closure string about retrieval bag 224, cartridge 208 may include cutting/shearing features that sever retrieval bag 224 from shells 228, 236 when shells 228, 236 are moved back from the open configuration to the closed configuration, such that retrieval bag 224 is separated from cartridge 208 when shells 228, 236 are moved from the open configuration to the closed configuration. In some such versions, a closure string may be positioned below the region at which retrieval bag 224 is cut, allowing retrieval bag 224 to remain closed by the closure string after retrieval bag 224 is severed from shells 228, 236 and allowing the closure string to remain uncut after retrieval bag 224 is severed from shells 228, 236. Still other suitable ways in which cartridge 208 and/or retrieval bag 224 may be removed from a patient will be apparent to those of ordinary skill in the art in view of the teachings herein.

While the above description provides adequate disclosure to enable one of ordinary skill in the art to make and use the versions of the specimen retrieval instrument shown and described in FIGS. 6-9, based on the teachings herein, those of ordinary skill in the art will appreciate that various modifications may provide additional features or functionality. For instance, in some versions modifications may prevent inadvertent extension or rotation of actuating rod 204 and premature opening of cartridge 208 and retrieval bag 224. For example, actuating rod 204 may include a lock or stop that may be released once a user is ready to open cartridge 208 and retrieval bag 224. Other suitable ways in which the specimen retrieval instrument may be configured to prevent inadvertent extension of actuating rod 204, inadvertent rotation of actuating rod 204, and/or premature opening of cartridge 208 and retrieval bag 224 will be apparent to those of ordinary skill in the art in view of the teachings herein.

In some versions, cartridge 208 may be available in various sizes having various sized retrieval bags 224. A surgeon may thus select a particular cartridge 108 from a supply of various cartridges 208 having differently sized retrieval bags 224, to select a retrieval bag 224 that is most appropriate or otherwise desired for a particular procedure or setting. In such versions, the desired sized cartridge 208 and retrieval bag 224 may be attached to actuating rod 204 and/or introducer tube 206 prior to insertion of the specimen retrieval instrument within a patient. Various suitable ways in which cartridge 208 may be removably coupled with specimen retrieval instrument to provide such modularity will be apparent to those of ordinary skill in the art in view of the teachings herein. Still various other suitable features, components, configurations, and operabilities that may be incorporated into the specimen retrieval instrument of FIGS. 6-9 will be apparent to those of ordinary skill in the art in view of the teachings herein.

II. Retrieval Bag with Cam Actuator

Referring now to FIGS. 10-16, another exemplary specimen retrieval instrument 300 is shown. Specimen retrieval instrument 300 of this example includes a handle assembly 302, an actuating rod 304, an introducer tube 306, a retrieval bag 324, a plug 334, a first support arm 336, a second support arm 338, and a cam actuator 308. Handle assembly 302, actuating rod 304, and introducer tube 306 of this example are configured and operable similarly to the corresponding components in FIGS. 1-5. Of course, each of these components may alternatively have any other suitable configuration and/or operability. The configuration and operation of these components with retrieval bag 324, first and second support arms 336, 338, and cam actuator 308 will be discussed in detail below.

Figure 10:
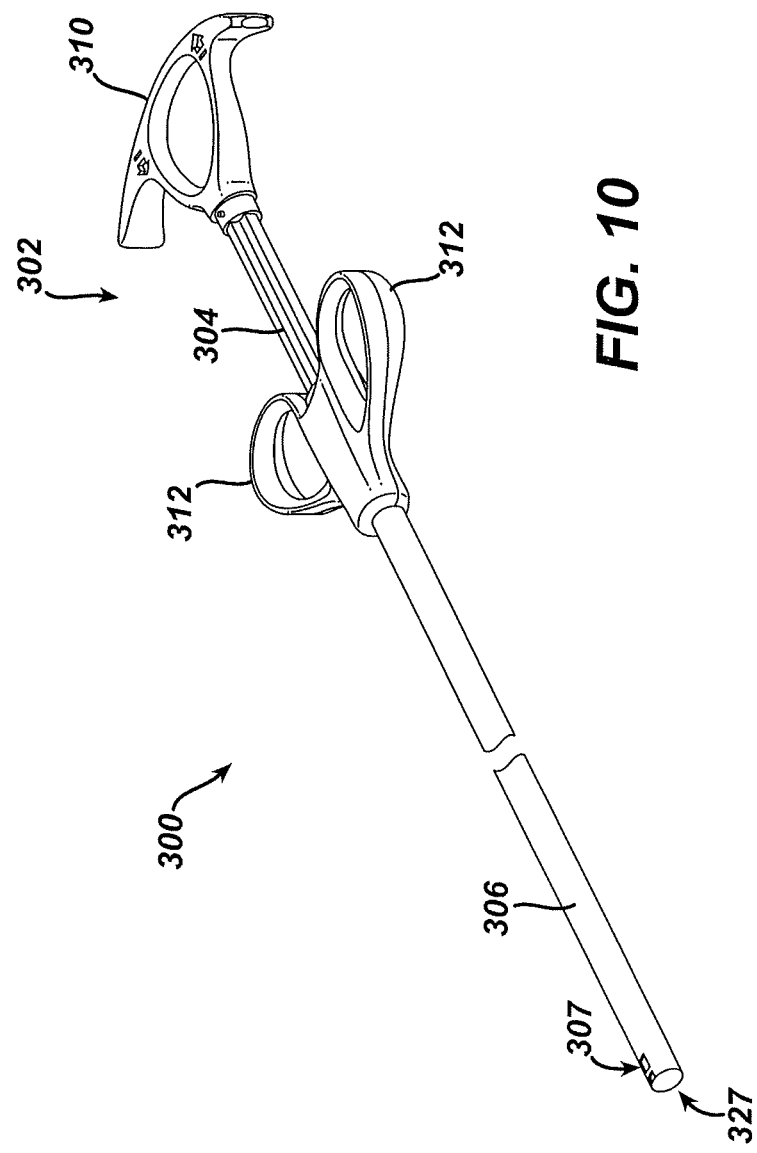
FIG. 10 is a perspective view of another exemplary specimen retrieval instrument, having a cam actuator for opening and closing the retrieval bag, with the retrieval bag shown retracted within the introducer tube.

As shown in FIG. 10, specimen retrieval instrument 300 is in an initial, fully retracted position. In this position, retrieval bag 324, first and second support arms 336, 338, cam actuator 308, and plug 334 are located within introducer tube 306. This position is achieved by thumb ring 310 being at a proximal position relative to finger rings 312 of handle assembly 302.

Figure 11:
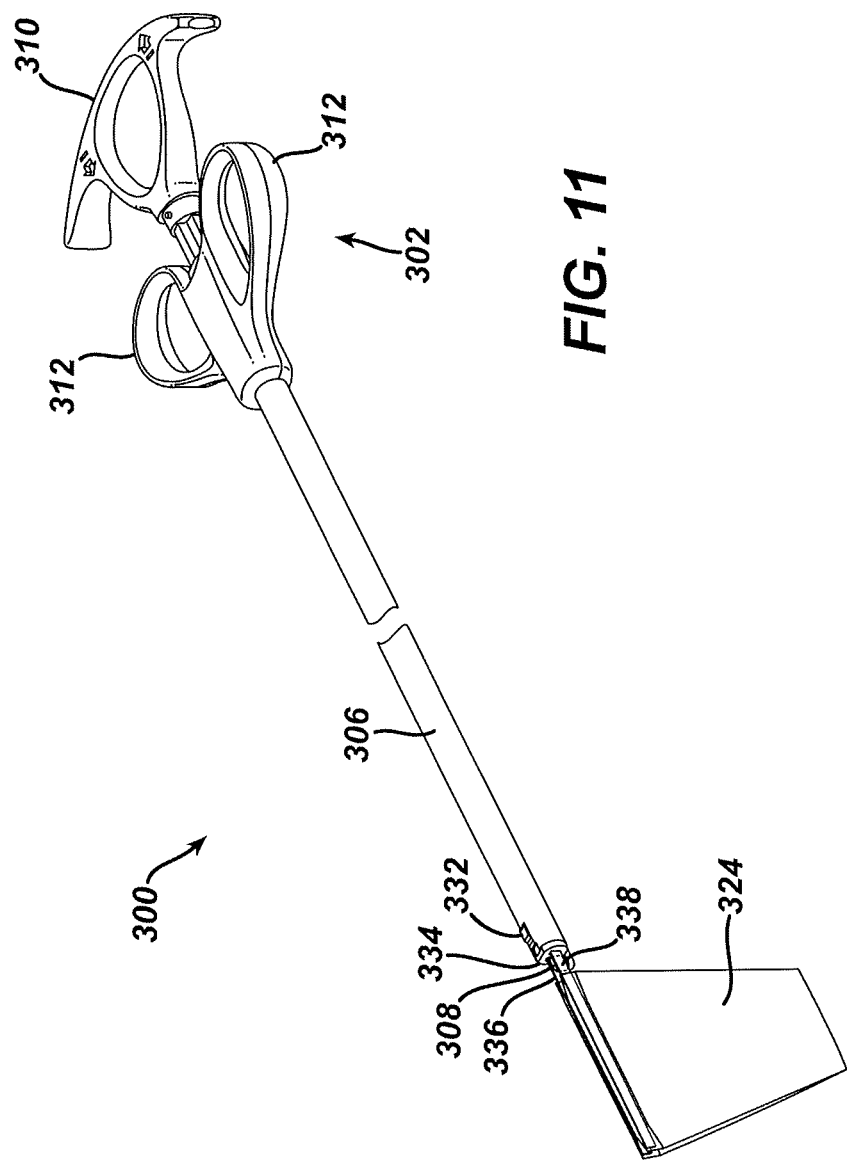
FIG. 11 is a perspective view of the specimen retrieval instrument of FIG. 10, with the retrieval bag deployed but in the closed position.

Referring to FIG. 11, specimen retrieval instrument 300 is shown with retrieval bag 324, first and second support arms 336, 338, cam actuator 308, and plug 334 deployed but with retrieval bag 324 closed. This position is achieved by thumb ring 310 being extended to a first distal position from the initial proximal position.

Figure 12:
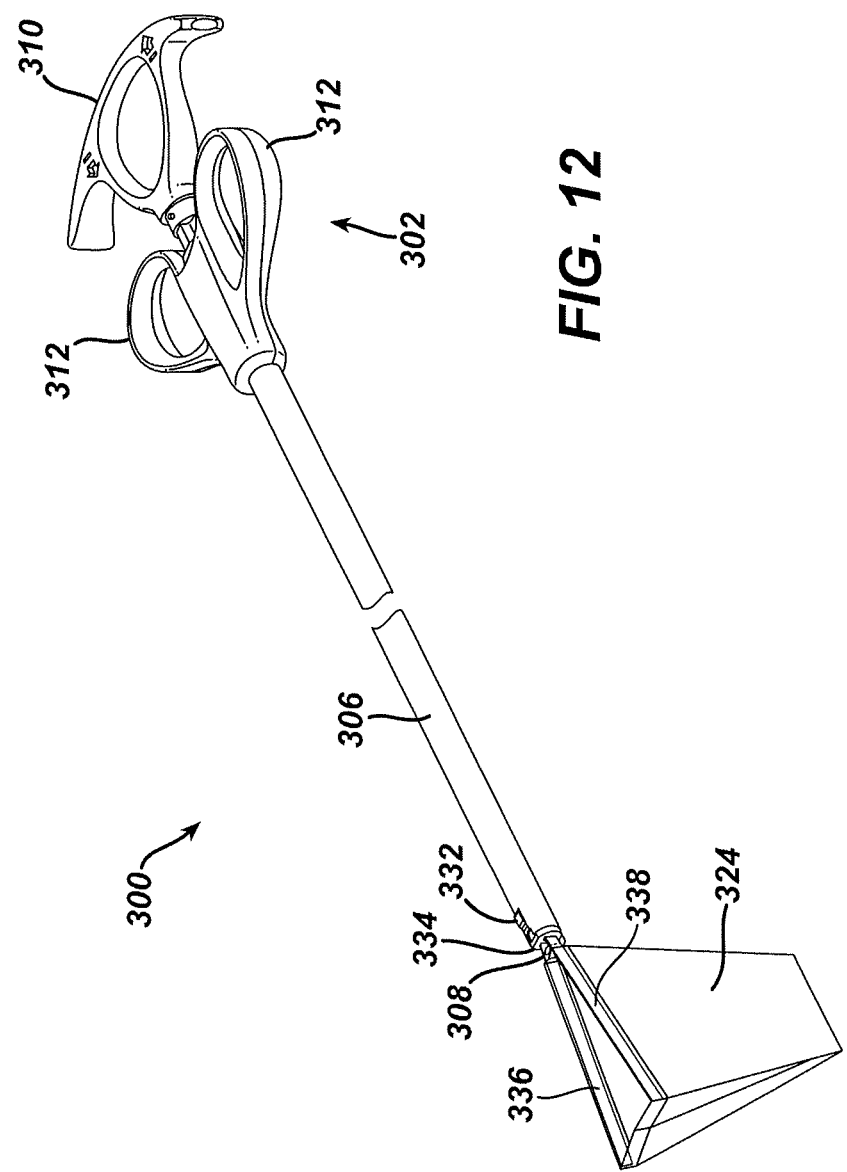
FIG. 12 is a perspective view of the specimen retrieval instrument of FIG. 10, with the retrieval bag deployed and in the open position.

Referring to FIG. 12, specimen retrieval instrument 300 is shown with retrieval bag 324, first and second support arms 336, 338, cam actuator 308, and plug 334 deployed and with retrieval bag 324 opened. This position is achieved by thumb ring 310 being extended further distally, to a second distal position, from the first distal position shown in FIG. 11.

Figure 13:
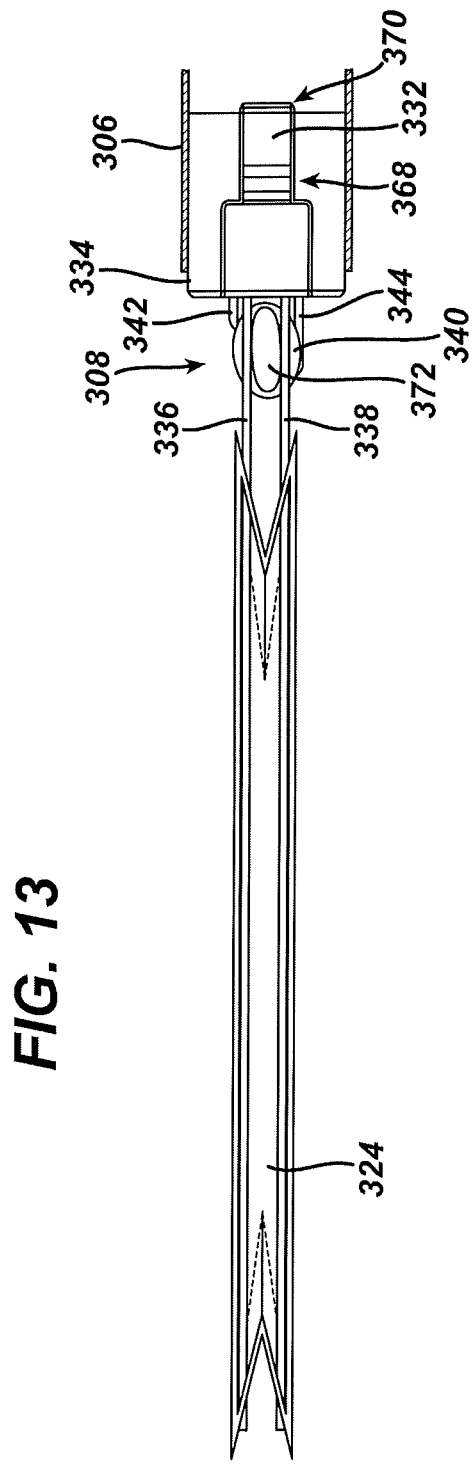
FIG. 13 is a top view of the distal end of the specimen retrieval instrument of FIG. 10 showing the cam actuator with the retrieval bag deployed and in the closed position and the introducer tube in cross section.
Figure 15:
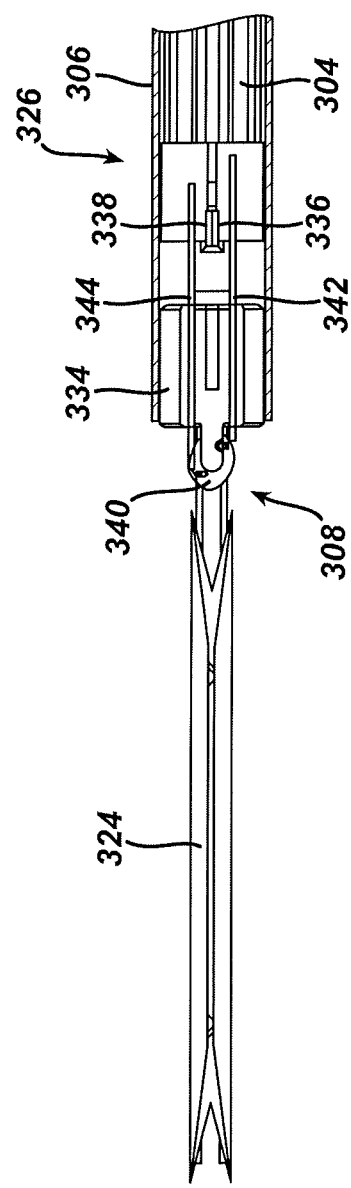
FIG. 15 is a bottom view of the specimen retrieval instrument of FIG. 10 showing the cam actuator with the retrieval bag deployed and in the closed position and the introducer tube in cross section.
Figure 16:
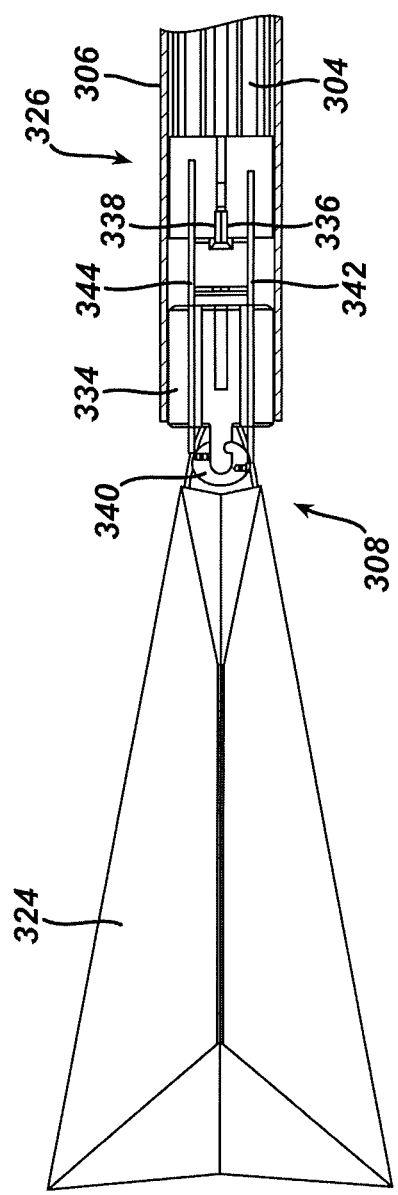
FIG. 16 is a bottom view of the specimen retrieval instrument of FIG. 10 showing the cam actuator with the retrieval bag deployed and in the open position and the introducer tube in cross section.

Referring to FIGS. 15 and 16, actuating rod 304 is positioned within introducer tube 306, and is translatably moveable relative to introducer tube 306 by movement of thumb ring 310 as discussed above. Actuating rod 304 includes distal end 326, which is connected to first and second support arms 336, 338 and plug 334. Support arms 336, 338 are secured to plug 334, and are resiliently biased to assume a closed position as shown in FIGS. 11, 13, and 15. By way of example only, support arms 336, 338 may be formed of a resilient metal, a resilient plastic, metal reinforced plastic, and/or any other suitable materials or combination of materials having any suitable properties. In the present example, support arms 336, 338 each comprise a single unitary piece of material without joints or breaks. However, in some other versions, one or more of support arms 336, 338 may comprise a segmented construction. In some such versions, one or more of support arms 336, 338 may comprise a single piece of material incorporating one or more hinges or flex points, including but not limited to living hinges, configured to allow that particular support arm 336, 338 to transition between the storage configuration and the desired expanded configuration. In some other versions, one or more of support arms 336, 338 may comprise at least two separate components hinged or connected together to allow that particular support arm 336, 338 to transition between the storage configuration and the desired expanded configuration. Still other suitable alternative configurations for support arms 336, 338 will be apparent to those of ordinary skill in the art in view of the teachings herein.

In the present example, the connection of distal end 326 of actuating rod 304 to first and second support arms 336, 338 is such that support arms 336, 338 move in unison with actuating rod 304 as actuating rod is moved from the proximal position shown in FIG. 10 to the first distal position shown in FIG. 11. As will be discussed further below, the connection of distal end 326 of actuating rod 304 to plug 334 is such that plug 334 may translate with actuating rod 304 to some extent (e.g., as actuating rod 304 is moved from the proximal position to the first distal position); but also such that actuating rod 304 may translate relative to plug 334 to some extent (e.g., as actuating rod 304 is moved from the first distal position to the second distal position).

As also shown in FIGS. 15 and 16, distal end 326 of actuating rod 304 is associated with cam actuator 308. More specifically, cam actuator 308 includes first and second actuating arms 342, 344 that extend proximally and longitudinally from the underside of cam body 340 to the underside of distal end 326 of actuating rod 304. Both actuating arms 342, 344 are pivotally attached to the underside of cam body 340. For example, the respective distal ends of actuating arms 342, 344 may extend upwardly and fit within corresponding receiving holes (not shown) in cam body 340. Further, first actuating arm 342 is securely attached to the underside of distal end 326 of actuating rod 304. However, second actuating arm 344 is translatable relative to actuating rod 304. Furthermore, cam body 340 is pivotally connected with plug 334—e.g. an upwardly extending post (not shown) of plug 334 may fit within a receiving hole (not shown) of cam body 340. Cam body 340 is thus rotatable about an axis that is transverse to the longitudinal axis defined by introducer tube 306 in the present example. As discussed in greater detail below, once retrieval bag 324 has been deployed to the position shown in FIG. 11, cam body 340 will pivot about the upwardly extending post of plug 334 as actuating rod longitudinally translates further distally, which in turn moves retrieval bag 324 from a closed position as shown in FIGS. 11, 13, and 15, to an open position as shown in FIGS. 12, 14, and 16.

Figure 14:
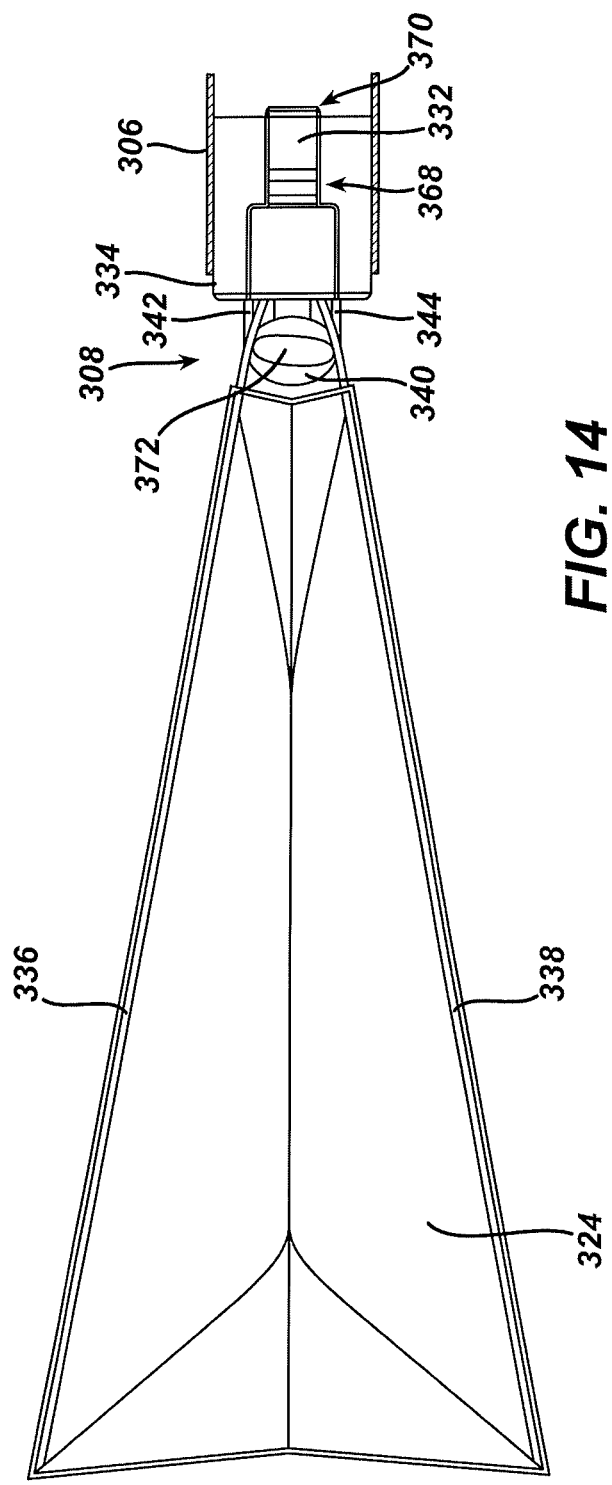
FIG. 14 is a top view of the distal end of the specimen retrieval instrument of FIG. 10 showing the cam actuator with the retrieval bag deployed and in the open position and the introducer tube in cross section.

Referring to FIGS. 13 and 14, cam body 340 may also include a projection 372. Projection 372 extends upwardly from the top of cam body 340 and is registered between first and second support arms 336, 338. Further, projection 372 has an elongated shape, e.g. an oval or elliptical shape as shown in FIGS. 13 and 14, or any other suitable elongated shape. With the elongated shape, as cam body 340 pivots about post of plug 334, projection 372 correspondingly rotates and cammingly acts on first and second support arms 336, 338. More specifically, as shown in FIG. 13, cam actuator 308 is in a closed position and the length of projection 372 is generally aligned with the length of first and second support arms 336, 338. Referring now to FIG. 14, cam actuator 308 has been rotated to an open position and the length of projection 372 is generally perpendicular to the length of first and second support arms 336, 338. As can be seen in comparing FIGS. 13 and 14, this pivoting action of cam body 340 and projection 372 act on first and second support arms 336, 338 to open and close them. In particular, rotating cam body 340 (and, hence, projection 372) to the position shown in FIG. 14 spreads support arms 336, 338 apart, against the resilient bias of support arms to assume a generally parallel orientation. Retrieval bag 324 is attached to first and second support arms 336, 338 such that retrieval bag 324 opens and closes with the opening and closing of support arms 336, 338. For instance, support arms 336, 338 may be inserted through corresponding slots or pockets (not shown) or other features adjacent to a top opening defined by retrieval bag 324.

As mentioned above, plug 334 is positioned distal to actuating rod 304 and is spaced apart from actuating rod 304. Plug 334 is slidably positioned within introducer tube 306 as can been seen in FIGS. 13-16. In some versions, the proximal ends of support arms 336, 338 are secured to distal end 326 of actuating rod 304, and support arms 336, 338 extend through corresponding openings (not shown) formed through plug 334. Alternatively, support arms 336, 338 may be secured to plug 334 or some other structure instead of being secured to distal end 326 of actuating rod 304. Plug 334 further includes tab 332 projecting upwardly from plug 334. A recess (not shown) is formed below tab 332 in plug 334. Tab 332 is resiliently biased to project upwardly from plug 334, but under sufficient force, tab 332 may be pushed downward to occupy at least part of the recess.

Tab 332 is configured to secure plug 334 by engaging opening 307 in introducer tube 306, when tab 332 is positioned within introducer tube 306 and aligned with opening 307. Tab 332 includes distal end 368 and proximal end 370. Distal end 368 of tab 332 is sloped while proximal end 370 is generally square. The generally square configuration of proximal end 370 may provide that, once retrieval bag 324 is deployed from within introducer tube 306, retrieval bag 324 cannot be retracted within introducer tube 306 without first depressing tab 332 such that tab 332 occupies its recess and disengages opening 307. The sloped configuration of distal end 368 allows tab 332 to be pressed downward within the recess by the inner diameter of introducer tube 306 when plug 334 is at a proximal position and during distal movement of plug 334. In some versions, opening 307 of introducer tube 306 may be slightly larger than tab 332 such that further distal or proximal movement of actuating rod 304 may permit slight corresponding distal or proximal movement of plug 334 even when tab 332 is in engagement with opening 307. In some versions, introducer tube 306 may also be provided with a distal locking member, which may be configured to abut a distal end of plug 334 such that the distal locking member prevents plug 334 from exiting introducer tube 306 during deployment and opening of retrieval bag 324.

In some versions, a coil spring (not shown) or other type of resilient member couples plug 334 with distal end 326 of actuating rod 304. For instance, such a coil spring may be positioned between plug 334 and distal end 326 of actuating rod 304, and may be biased to maintain spatial separation between plug 334 and distal end 326 of actuating rod 304. Such a coil spring may also have a spring constant that is sufficient to substantially maintain this spatial separation as actuating rod 304 is moved from a proximal position as shown in FIG. 10 to a first distal position as shown in FIG. 11, despite any friction between plug 334 and the inner diameter of introducer tube 306. Such a coil spring may thus provide substantially unitary translation of plug 334 with actuating rod 304 as actuating rod 304 is moved from a proximal position as shown in FIG. 10 to a first distal position as shown in FIG. 11. However, upon plug 334 reaching the first distal position, tab 332 of plug 334 snaps into opening 307 of introducer tube 306 in the present example. This engagement between tab 332 and opening 307 restricts further distal movement of plug 334. Accordingly, as actuating rod 304 continues to advance distally in introducer tube 306 (e.g., from the first distal position shown in FIG. 11 to the second distal position shown in FIG. 12), plug 334 remains substantially stationary in introducer tube 306 and the coil spring compresses. This additional distal movement of actuating rod 304 relative to plug 334 and introducer tube 306 actuates cam body 340 to open retrieval bag 324 as described in greater detail below.

In use, specimen retrieval instrument 300 may initially have the arrangement shown in FIG. 10, where retrieval bag 324 is disposed within introducer tube 306, and thumb ring 310 and actuating rod 304 are at a proximal position. In this arrangement, the distal portion of specimen retrieval instrument 300 may be inserted within a patient through a suitable incision opening or access port created by a trocar or some other device. Once positioned within the patient, retrieval bag 324 may be deployed from within introducer tube 306 by pushing thumb ring 310 distally toward finger rings 312 to the first distal position shown in FIG. 11. This action drives actuating rod 304 and plug 334 distally, causing retrieval bag 324, first and second support arms 336, 338, and cam actuator 308 to emerge from open distal end 327 of introducer tube 306. At about the same time retrieval bag 324 is deployed, tab 332 of plug 334 aligns with opening 307 of introducer tube 306, substantially securing the longitudinal position of plug 334 within introducer tube 306. When aligned, tab 332 engages opening 307 due to tab 332 being resiliently biased to project upwardly from plug 334. Once retrieval bag 324 has been deployed, specimen retrieval instrument 300 may have the arrangement shown in FIGS. 11, 13, and 15.

With specimen retrieval instrument 300 in position within the patient and having retrieval bag 324 deployed, thumb ring 310 is pushed further distally, driving actuating rod 304 further distally to the second distal position shown in FIG. 12. This further distal movement of actuating rod 304 causes first actuating arm 342 to translate distally while cam body 340 pivots about the post of now stationary plug 334. This pivoting action of cam body 340 drives second actuating arm 344 proximally. Plug 334, introducer tube 306, and/or distal end 326 of actuating rod 304 may include a channel (not shown) in which second actuating arm 344 is slidably disposed; and which guides second actuating arm 344 as second actuating arm 344 translates proximally. In some versions, second actuating arm 344 is simply omitted. The shape of projection 372 of cam body 340 and the pivoting action force support arms 336, 338 to open or spread apart and thus open attached retrieval bag 324.

In some versions retrieval bag 324 is maintained in an open position by thumb ring 310 being configured to remain at a fully distal position. Some such versions may use various biasing or locking means (e.g., releasable ratcheting mechanism, etc.) to accomplish this, while in other versions this may not be necessary. Still in other versions, thumb ring 310 may be biased to seek the intermediate position or first distal position where the bag is deployed but closed. In some such versions it may be necessary to hold thumb ring 310 in its fully distal position to maintain retrieval bag 324 in an open position. In any of these versions, when retrieval bag 324 is open, a specimen can be placed within.

Once a specimen has been placed within retrieval bag 324, thumb ring 310 may be retracted, thereby causing first actuating arm 342 to be retracted proximally and cam body 340 to pivot about post of plug 334 to its closed position as shown in FIG. 13. Due to the resilient bias of support arms 336, 338 in this example, this action of cam body 340 causes support arms 336, 338 to return to their closed position and consequently also close retrieval bag 324. From this point, specimen retrieval instrument 300, including retrieval bag 324 and specimen, may be removed from the patient. In some versions, retrieval bag 324 maybe be removed from the patient at or about the same time with the other components of specimen retrieval instrument 300.

In some other versions, specimen retrieval instrument 300 is configured such that retrieval bag 324 may be removed from specimen retrieval instrument 300 while retrieval bag 324 is within the patient. Some such versions facilitate removal of retrieval bag 324 separate from removal of the other components of specimen retrieval instrument 300. In some versions, this may be accomplished by, among other ways, retrieval bag 324 being removable from first and second support arms 336, 338. For instance, in some versions specimen retrieval instrument 300 may include a closure string connected to retrieval bag 324 and having a slipknot attachment to actuating rod 304. Pulling the slipknot loose and retracting the actuating rod 304 may permit detachment of retrieval bag 324 and the closure string from the other components of specimen retrieval instrument 300. In some such versions, a user may pull the closure string to close retrieval bag 324. By way of example only, such a closure mechanism may be configured in accordance with the teachings of U.S. Pat. No. 6,409,733, entitled "Specimen Retrieval Bag," issued Jun. 25, 2002, which is incorporated herein by reference. Still in other versions, it may be feasible to incorporate a closure string with retrieval bag 324, and to release retrieval bag 324 from specimen retrieval instrument 300 such that retrieval bag 324 may be removed from the patient separate from other components of specimen retrieval instrument 300.

While the above description provides adequate disclosure to enable one of ordinary skill in the art to make and use specimen retrieval instrument 300, based on the teachings herein, those of ordinary skill in the art will appreciate that various modifications may provide additional features or functionality. For instance, in some versions, actuating rod 304 may comprise features operable with other features of introducer tube 306 or other components to prevent inadvertent retraction of actuating rod 304 during retrieval bag 324 deployment. For example, actuating rod 304 may include a one way ratcheting mechanism as described in U.S. Pat. No. 6,409,733, entitled "Specimen Retrieval Bag," issued Jun. 25, 2002, which is incorporated herein by reference. Other ways in which inadvertent retraction of actuating rod 304 may be avoided through various features of specimen retrieval instrument will be apparent to those of ordinary skill in the art in view of the teachings herein.

While actuating arm 342 is actuated by actuating rod 304 in the present example, it should be understood that actuating arm 342 may be actuated in various other ways. By way of example only, a separate actuator (e.g., rod, push/pull cable, etc.) may be coupled with actuating arm 342, with such a separate actuator being operable independently of actuating rod 304. In some such versions, actuating rod 304 and plug 334 may be integral or unitary, such that there is no opportunity for relative movement between actuating rod 304 and plug 342 during normal operation of specimen retrieval instrument 300. As another merely illustrative alternative, an actuator may be operable to actively pull actuating arm 344 to open retrieval bag 324, in addition to or in lieu of actuating rod 304 being operable to push actuating arm 342 to open retrieval bag 324. Various other suitable ways in which cam body 340 may be rotated will be apparent to those of ordinary skill in the art in view of the teachings herein.

It should also be understood that specimen retrieval instrument 300 may be configured such that thumb ring 310 may be pulled proximally to a degree sufficient to pull support arms 336, 338 completely through plug 334 after plug 334 has been "locked" to the distal-most position by engagement of tab 332 in opening 307. In some such versions, the engagement between distal end 326 of actuating rod 304 and actuating arm 342 may permit actuating rod 304 to disengage from actuating arm 342 when actuating rod 304 is pulled proximally. Still various other suitable features, components, configurations, and operabilities that may be incorporated into specimen retrieval instrument 300 will be apparent to those of ordinary skill in the art in view of the teachings herein.

III. Retrieval Bag with Rotating Curved Support Arms

Referring to FIGS. 17-21, another exemplary specimen retrieval instrument 400 is shown. Specimen retrieval instrument 400 of this example includes a handle assembly 402, an actuating rod 404, an introducer tube 406, a retrieval bag 424, a plug 434, a first support arm 436, and a second support arm 438. Handle assembly 402, actuating rod 404, and introducer tube 406 may be configured similarly to the corresponding components in FIGS. 1-5. Of course, each of these components may alternatively have any other suitable configuration and/or operability. The configuration and operation of these components with the retrieval bag and first and second support arms 436, 438 will be discussed in detail below.

Specimen retrieval instrument 400 is initially in a fully retracted position (not shown). In this position, retrieval bag 424, first and second support arms 436, 438, the retrieval bag, and plug 434 are located within introducer tube 406. This position is achieved by thumb ring 410 being at a proximal position relative to finger rings 412 of handle assembly 402. In this configuration, specimen retrieval instrument 400 may look substantially identical to specimen retrieval instrument 300 shown in FIG. 10.

Figure 17:
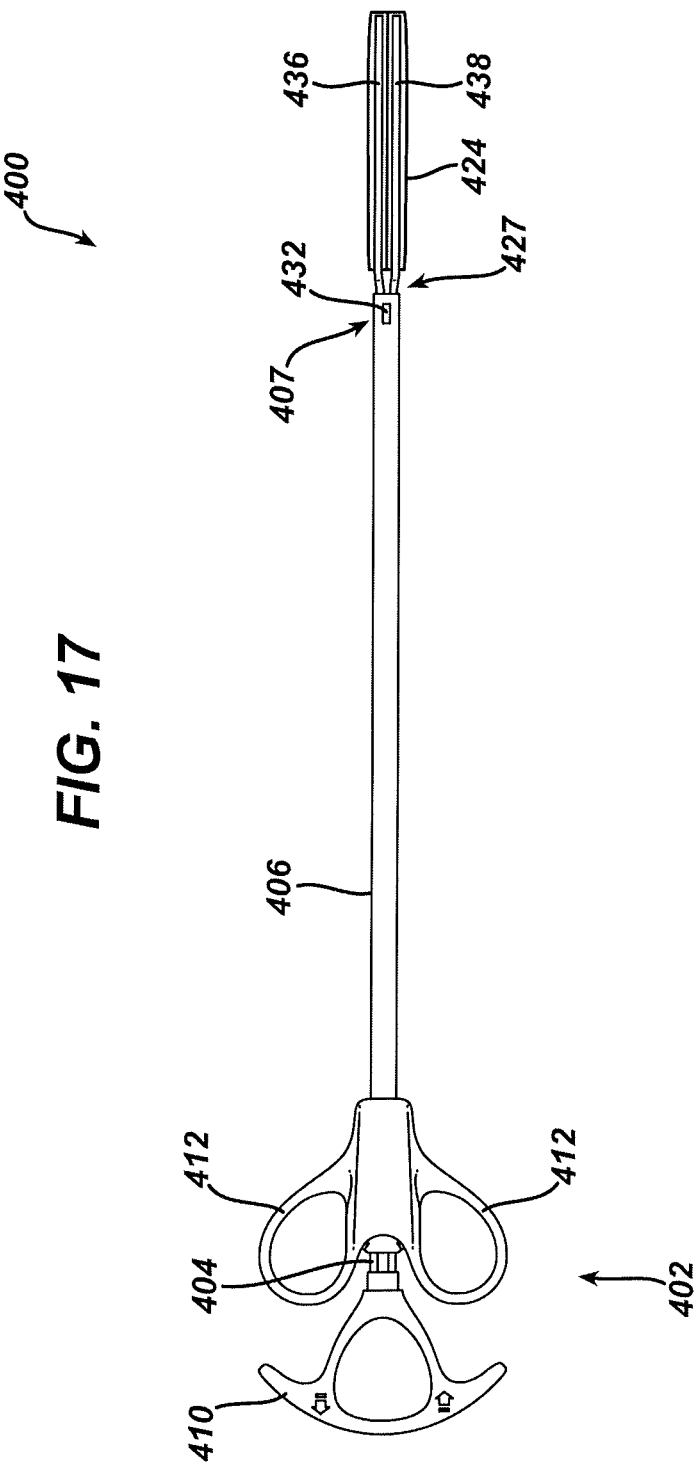
FIG. 17 is a top view of another exemplary specimen retrieval instrument, having a pair of rotating curved arms for opening and closing the retrieval bag, with the arms deployed and in their closed position.
Figure 18:
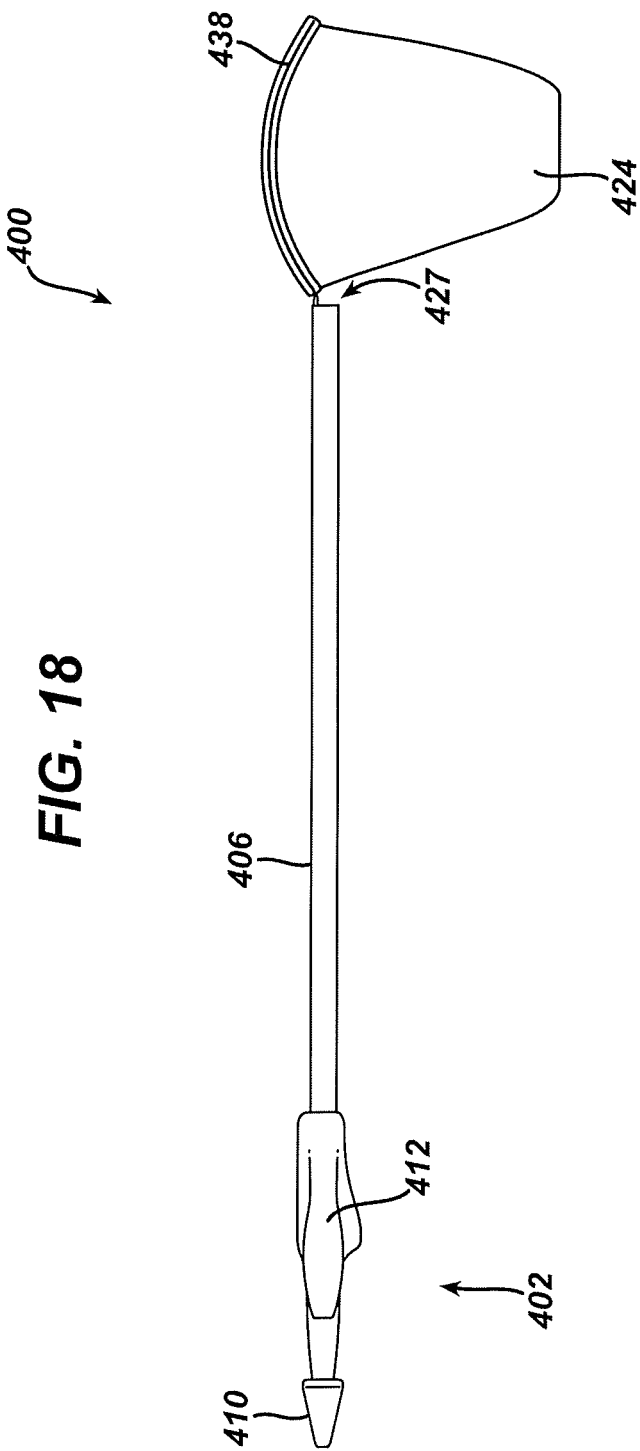
FIG. 18 is a side view of the specimen retrieval instrument of FIG. 17 showing the curvature of the arms.
Figure 20:
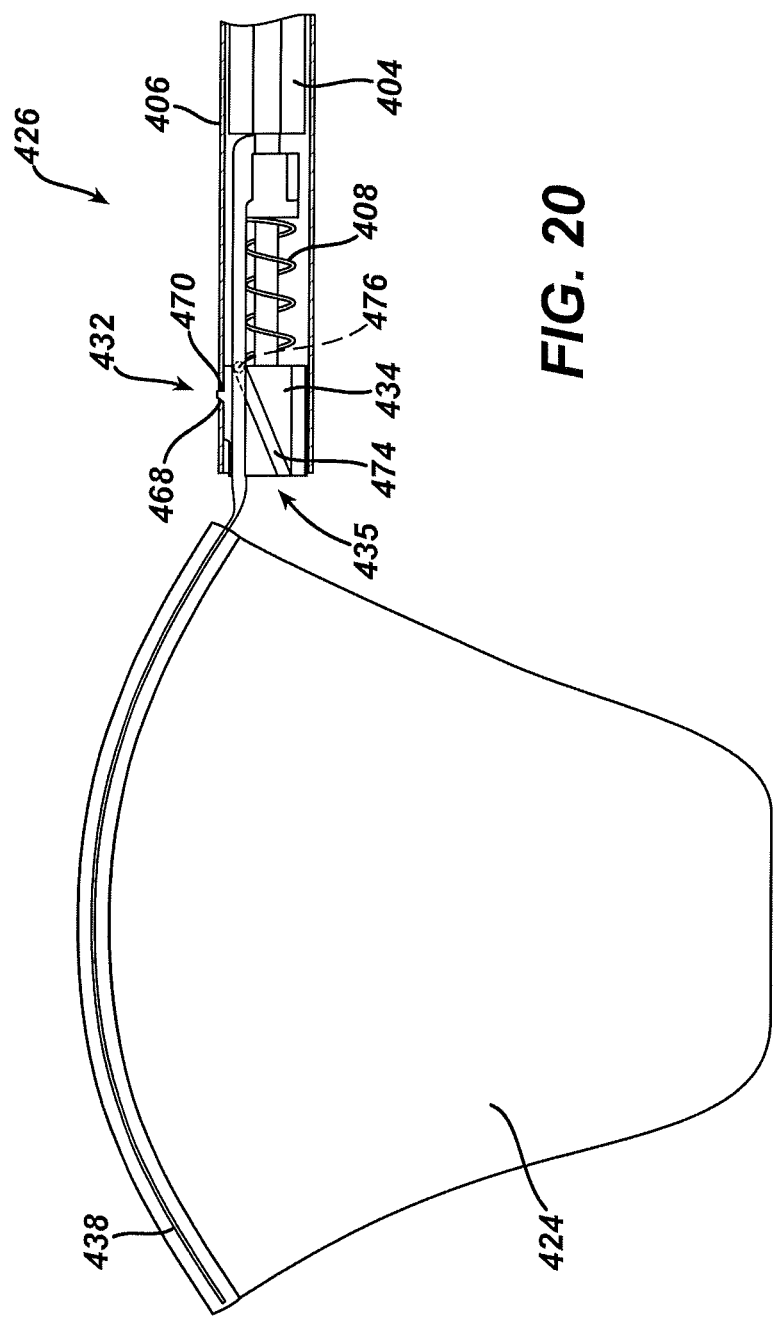
FIG. 20 is a side view of the distal end of the specimen retrieval instrument of FIG. 17, with the arms deployed and in their closed position with the retrieval bag omitted and the introducer tube in cross section.

Referring to FIGS. 17-18 and 20, specimen retrieval instrument 400 is shown with first and second support arms 436, 438 and plug 434 deployed. In this configuration, the retrieval bag but with retrieval bag 424 closed. This position is achieved by thumb ring 410 being extended to a first distal position from the initial proximal position. As shown in FIGS. 18 and 20, first and second support arms 436, 438 are curved. However, first and second support arms 436, 438 are flexible enough to substantially flatten when support arms 436, 438 are fully retracted within introducer tube 406. In some versions, support arms 436, 438 are resiliently biased to assume the curved configuration shown in FIGS. 18 and 20. By way of example only, support arms 436, 438 may be formed of a resilient metal, a resilient plastic, metal reinforced plastic, and/or any other suitable materials or combination of materials having any suitable properties. In the present example, support arms 436, 438 each comprise a single unitary piece of material without joints or breaks. However, in some other versions, one or more of support arms 436, 438 may comprise a segmented construction. In some such versions, one or more of support arms 436, 438 may comprise a single piece of material incorporating one or more hinges or flex points, including but not limited to living hinges, configured to allow that particular support arm 436, 438 to transition between the storage configuration and the desired expanded configuration. In some other versions, one or more of support arms 436, 438 may comprise at least two separate components hinged or connected together to allow that particular support arm 436, 438 to transition between the storage configuration and the desired expanded configuration. Still other suitable alternative configurations for support arms 436, 438 will be apparent to those of ordinary skill in the art in view of the teachings herein.

Figure 19:
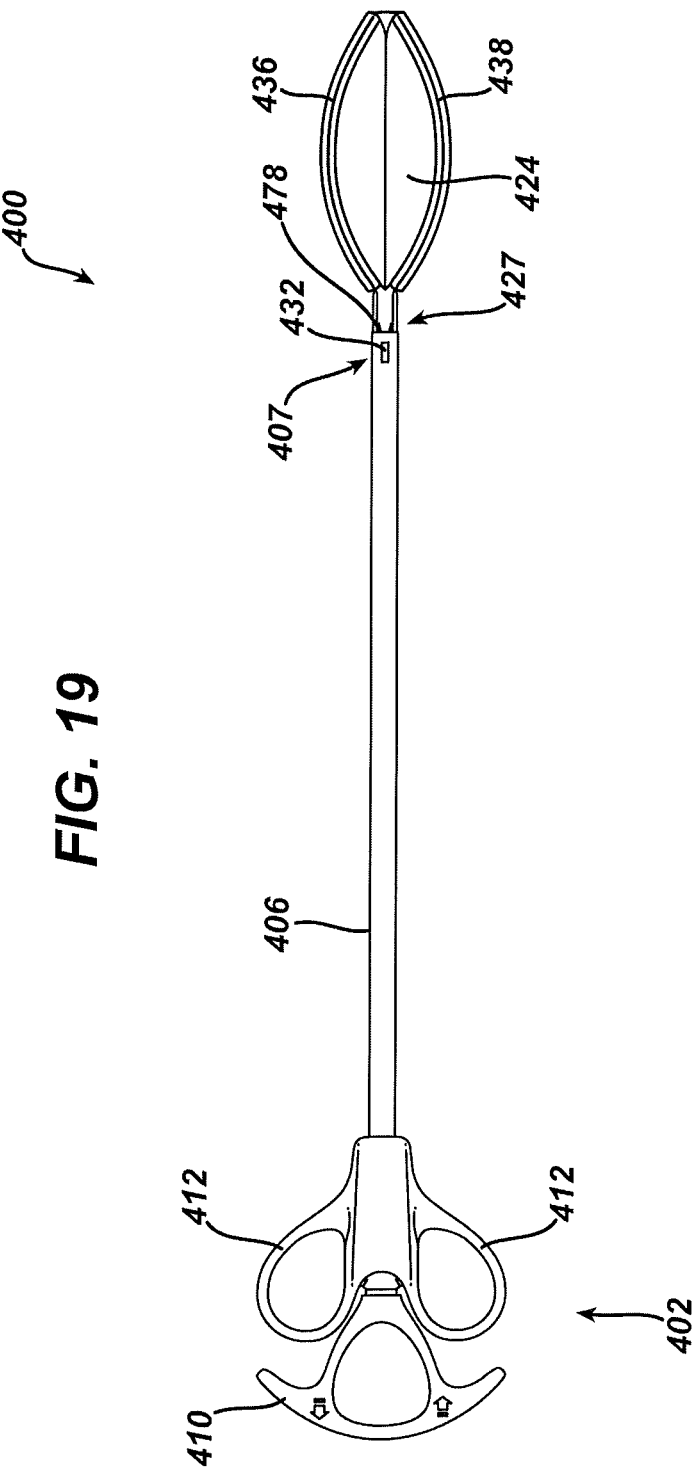
FIG. 19 is a top view of the specimen retrieval instrument of FIG. 17, with the arms deployed and in their open position.
Figure 21:
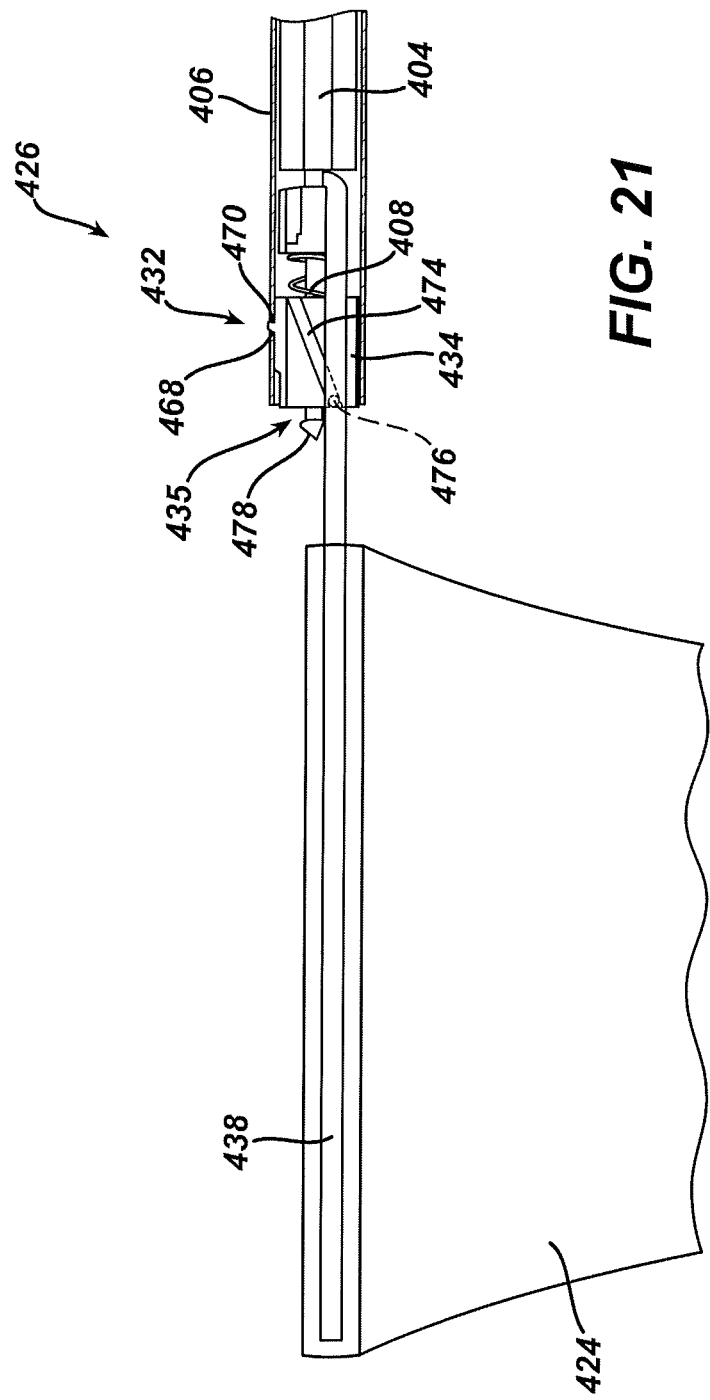
FIG. 21 is a side view of the distal end of the specimen retrieval instrument of FIG. 17, with the arms deployed and in their open position with the retrieval bag omitted and the introducer tube in cross section.

Referring to FIGS. 19 and 21, specimen retrieval instrument 400 is shown with retrieval bag 424, first and second support arms 436, 438, and plug 434 deployed and with retrieval bag 424 opened. This position is achieved by thumb ring 410 being extended further distally, to a second distal position, from the first distal position shown in FIGS. 17-18 and 20.

Referring to FIGS. 20 and 21, actuating rod 404 is positioned within introducer tube 406, and is translatably moveable relative to introducer tube 406 by movement of thumb ring 410 as discussed above. Actuating rod 404 includes distal end 426, which is connected to first and second support arms 436, 438 such that support arms 436, 438 translate in unison with actuating rod 404. Distal end 426 is also coupled plug 434. However, the connection of distal end 426 of actuating rod 404 to plug 434 is such that plug 434 may translate with actuating rod 404 to some extent (e.g., as actuating rod 404 is moved from the proximal position to the first distal position); but also such that actuating rod 404 may translate relative to plug 434 to some extent (e.g., as actuating rod 404 is moved from the first distal position to the second distal position). In particular, as shown in FIGS. 20 and 21, plug 434 of the present example includes an opening 435, and a portion of distal end 426 is configured to fit through opening 435. Additionally, and as will be described in greater detail below, a spring 408 is positioned proximal of plug 434 and contacting both plug 434 and actuating rod 404. First and second support arms 436, 438 are also movably connected with plug 434. For example, as shown in FIGS. 20 and 21, plug 434 includes a groove 474 on each side of plug 434. A pair of retaining pins 476 are coupled with first and second support arms 436, 438 and also fit within grooves 74 as will be described in greater detail below. In particular, each support arm 436, 438 has a respective pin 476 that is registered within a corresponding groove 74 of plug 434. Retrieval bag 424 is attached to first and second support arms 436, 438 such that retrieval bag 424 opens and closes with the opening and closing of support arms 436, 438. For instance, support arms 436, 438 may be inserted through corresponding slots or pockets (not shown) or other features adjacent to a top opening defined by retrieval bag 424.

As mentioned above, plug 434 is positioned distal from actuating rod 404 and is spaced apart from actuating rod 404. Plug 434 is slidably positioned within introducer tube 406 as can be seen in FIGS. 17-21. In addition to opening 435 and grooves 474 discussed above, plug 434 further includes tab 432 projecting upwardly from plug 434. A recess (not shown) is formed below tab 432 in plug. Tab 432 is resiliently biased to project upwardly from plug 434, but under sufficient force, tab 432 may be pushed downward to occupy at least part of the recess.

Tab 432 is configured to secure plug 434 by engaging opening 407 in introducer tube 406, when tab 432 is positioned within introducer tube 406 and aligned with opening 407. Tab 432 includes distal end 468 and proximal end 470. Distal end 468 of tab 432 is sloped while proximal end 470 is generally square. The generally square configuration of proximal end 470 may provide that, once retrieval bag 424 is deployed from within introducer tube 406, retrieval bag 424 cannot be retracted within introducer tube 406 without first depressing tab 432 such that tab 432 occupies its recess and disengages opening 407. The sloped configuration of distal end 468 allows tab 432 to be pressed downward within the recess by the inner diameter of introducer tube 406 when plug 434 is at a proximal position and during distal movement of plug 434. In some versions, opening 407 of introducer tube 406 may be slightly larger than tab 432 such that further distal or proximal movement of actuating rod 404 may permit slight corresponding distal or proximal movement of plug 434 even when tab 432 is in engagement with opening 407. In some versions, introducer tube 406 may also be provided with a distal locking member, which may be configured to abut a distal end of plug 434 such that the distal locking member prevents plug 434 from exiting introducer tube 406 during deployment and opening of retrieval bag 424.

As noted above, spring 408 couples plug 434 with actuating rod 404. Of course, any other suitable type of resilient member may be used. Alternatively, plug 434 may be coupled with actuating rod 404 in any other suitable fashion. Spring 408 is biased to maintain spatial separation between plug 434 and distal end 426 of actuating rod 404. Spring 408 may also have a spring constant that is sufficient to substantially maintain this spatial separation as actuating rod 404 is moved from a proximal position (e.g., similar to what is shown in FIG. 10) to a first distal position as shown in FIGS. 17-18 and 20, despite any friction between plug 434 and the inner diameter of introducer tube 406. Spring 408 may thus provide substantially unitary translation of plug 434 with actuating rod 404 as actuating rod 404 is moved from a proximal position (e.g., similar to what is shown in FIG. 10) to a first distal position as shown in FIGS. 17-18 and 20. However, upon plug 434 reaching the first distal position, tab 432 of plug 434 snaps into opening 407 of introducer tube 406 in the present example. This engagement between tab 432 and opening 407 restricts further distal movement of plug 434. Accordingly, as actuating rod 404 continues to advance distally in introducer tube 406 (e.g., from the first distal position shown in FIGS. 17-18 and 20 to the second distal position shown in FIGS. 19 and 21), plug 434 remains substantially stationary in introducer tube 406 and spring 408 compresses. This additional distal movement of actuating rod 404 relative to plug 434 and introducer tube 406 causes support arms 436, 438 to spread apart and thereby open retrieval bag 424 as described in greater detail below.

In use, specimen retrieval instrument 400 may initially have the arrangement where retrieval bag 424 is disposed within introducer tube 406, and thumb ring 410 and actuating rod 404 are at a proximal position (e.g., similar to what is shown in FIG. 10). In this arrangement, the distal portion of specimen retrieval instrument 400 may be inserted within a patient through a suitable incision opening or access port created by a trocar or some other device. Once positioned within the patient, retrieval bag 424 may be deployed from within introducer tube 406 by pushing thumb ring 410 distally toward finger rings 412 to the first distal position shown in FIGS. 17-18 and 20. This action drives actuating rod 404 and plug 434 distally causing retrieval bag 424 and first and second support arms 436, 438 to emerge from open distal end 427 of introducer tube 406. At about the same time retrieval bag 424 is deployed, tab 432 of plug 434 aligns with opening 407 of introducer tube 406, substantially securing the longitudinal position of plug 434 within introducer tube 406. When aligned, tab 432 engages opening 407 due to tab 432 being resiliently biased to project upwardly from plug 434. Once retrieval bag 424 has been deployed, specimen retrieval instrument 400 may have the arrangement shown in FIGS. 17-18 and 20.

With specimen retrieval instrument 400 in position within the patient and having retrieval bag 424 deployed, thumb ring 410 is pushed further distally, driving actuating rod 404 further distally to the second distal position shown in FIGS. 19 and 21. This further distal movement of actuating rod 404 causes spring 408 to compress against plug 434, which is now held generally stationary by engagement of tab 432 of plug 434 with opening 407 of introducer tube 406. As spring 408 compresses, first and second support arms 436, 438 are driven distally. At the same time, retaining pins 476 are guided along grooves 474 of plug 434. The shape of grooves 434 are configured in a spiral-like or helical fashion, such that as pins 476 move within grooves 474, first and second support arms 436, 438 rotate about a central axis defined by actuating rod 404 by approximately ninety degrees. This rotation of first and second support arms 436, 438 moves support arms 436, 438 from a closed position as shown in FIGS. 17-18, and 20 to an open position as shown in FIGS. 19 and 21. First and second support arms 436, 438 are further connected with retrieval bag 424 such that rotation of support arms 436, 438 causes retrieval bag 424 to move from a closed position to an open position.

In some versions retrieval bag 424 is maintained in an open position by thumb ring 410 being configured to remain at a fully distal position. Some such versions may use various biasing or locking means (e.g., releasable ratcheting mechanism, etc.) to accomplish this, while in other versions this may not be necessary. For example, as shown in FIGS. 19 and 21, actuating rod 404 may be configured to include locking member 478 at its distal most end. When actuating rod 404 is driven distally, to the second distal position, to open first and second support arms 436, 438, locking member 478 protrudes from opening 435 of plug 434 and expands. The expansion of locking member 478 is such that it is now too large to fit within opening 435 of plug 434 when actuating rod 404 is retracted. Thus, retrieval bag 424 would be locked in the open position. To retract actuating rod 404 proximally, locking member 478 may require disengagement by some other feature of specimen retrieval instrument 400 or by another instrument, e.g. a grasper. Still in other versions, thumb ring 410 may be biased to seek the intermediate position or first distal position where retrieval bag 424 is deployed but closed. In some such versions it may be necessary to hold thumb ring 410 in its fully distal position to maintain retrieval bag 424 in an open position. In any of these versions, when retrieval bag 424 is open, a specimen can be placed within.

Once a specimen has been placed within retrieval bag 424, thumb ring 410 may be retracted, thereby causing spring 408 to decompress and retaining pins 476 to move proximally within grooves 474 of plug 434. This action causes support arms 436, 438 to return to their closed position and consequently also close retrieval bag 424. From this point, specimen retrieval instrument 400, including retrieval bag 424 and specimen, may be removed from the patient. In some versions, retrieval bag 424 maybe be removed from the patient at or about the same time with the other components of specimen retrieval instrument 400.

In some other versions, specimen retrieval instrument 400 is configured such that retrieval bag 424 may be removed from specimen retrieval instrument 400 while retrieval bag 424 is within the patient. Some such versions facilitate removal of retrieval bag 424 separate from removal of the other components of specimen retrieval instrument 400. In some versions, this may be accomplished by, among other ways, retrieval bag 424 being removable from first and second support arms 436, 438. For instance, in some versions specimen retrieval instrument 400 may include a closure string connected to retrieval bag 424 and having a slipknot attachment to actuating rod 404. Pulling the slipknot loose and retracting the actuating rod 404 may permit detachment of retrieval bag 424 and the closure string from the other components of specimen retrieval instrument 400. In some such versions, a user may pull the closure string to close retrieval bag 424. By way of example only, such a closure mechanism may be configured in accordance with the teachings of U.S. Pat. No. 6,409,733, entitled "Specimen Retrieval Bag," issued Jun. 25, 2002, which is incorporated herein by reference. Still in other versions, it may be feasible to incorporate a closure string with retrieval bag 424, and to release retrieval bag 424 from specimen retrieval instrument 400 such that retrieval bag 424 may be removed from the patient separate from other components of specimen retrieval instrument 400.

While the above description provides adequate disclosure to enable one of ordinary skill in the art to make and use specimen retrieval instrument 400, based on the teachings herein, those of ordinary skill in the art will appreciate that various modifications may provide additional features or functionality. For instance, in some versions, actuating rod 404 may comprise features operable with other features of introducer tube 406 or other components to prevent inadvertent retraction of actuating rod 404 during retrieval bag 424 deployment. For example, actuating rod 404 may include a one way ratcheting mechanism as described in U.S. Pat. No. 6,409,733, entitled "Specimen Retrieval Bag," issued Jun. 25, 2002, which is incorporated herein by reference. Other ways in which inadvertent retraction of actuating rod 404 may be avoided through various features of specimen retrieval instrument will be apparent to those of ordinary skill in the art in view of the teachings herein. Still various other suitable features, components, configurations, and operabilities that may be incorporated into specimen retrieval instrument 300 will be apparent to those of ordinary skill in the art in view of the teachings herein.

As noted above, the various versions of specimen retrieval instruments described herein, including but not limited to the various versions of retrieval bags described herein, may be used in a conventional endoscopic procedure that includes the insertion of the introducer tube or other component through a small opening, e.g., an incision, natural orifice, or trocar access port, etc. Of course, specimen retrieval instruments described herein may be used in conjunction with any other suitable surgical or medical procedure, such as endoscopic/laparoscopic procedures, open surgical procedures, or robotic-assisted surgery, etc. Still other various settings and combinations in which specimen retrieval instruments described herein may be used will be apparent to those of ordinary skill in the art in view of the teachings herein.

While several specimen retrieval instruments, and components thereof, have been discussed in detail above, it should be understood that the components, features, configurations, and methods of using the specimen retrieval instruments discussed are not limited to the contexts provided above. In particular, components, features, configurations, and methods of use described in the context of one of the specimen retrieval instruments may be incorporated into any of the other specimen retrieval instruments. One merely exemplary additional feature that may be provided in any of the specimen retrieval instruments described herein includes retrieval bags having various sizes and geometries. For example, some specimen retrieval instruments may be designed with small, medium, or large retrieval bags. Also for example, some tissue retrieval instruments may use retrieval bags having pleats and/or gussets that allow for expansion when holding larger specimens. It should also be understood that any of the specimen retrieval instruments and tissue retrieval bags described herein may be capable of receiving tissue specimens and removing tissue specimens from a patient without such tissue specimens needing to be morcellated or otherwise reduced in size before being received and removed by the specimen retrieval instrument and bag. Still other additional and alternative suitable components, features, configurations, and methods of using the specimen retrieval instruments will be apparent to those of ordinary skill in the art in view of the teachings herein.

Other features and modifications that will be appreciated based on the teachings herein involve methods of attaching a retrieval bag to any of the various arms and loops or other components of a specimen retrieval instrument described above. For example, retrieval bags may be configured with one or more sleeves, slots, pockets, loops, slits, etc., for receiving any of the various arms and loops described above. In other versions, retrieval bags may be connected to any of the various arms, loops, or other components using suitable mechanical or chemical means. It will further be appreciated that in some versions the retrieval bag may be detachable from the other components of the specimen retrieval instrument, while in some other versions the retrieval bag may be inseparable from the specimen retrieval instrument. Still other additional and alternative suitable components, features, configurations, and methods of attaching retrieval bags with the other components of a specimen retrieval instrument will be apparent to those of ordinary skill in the art in view of the teachings herein.

It should also be understood that the components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While the specimen retrieval instruments of the above-described examples are actuated manually by advancing a thumb ring distally relative to finger rings or in some other manual fashion, etc., it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethyelene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the devices disclosed herein have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument for removal of a specimen from a patient, the surgical instrument comprising:
   a. a retrieval bag configured to open and close;
   b. a first arm comprising a distal end and a proximal end, wherein the first arm is associated with the retrieval bag;
   c. a second arm comprising a distal end and a proximal end, wherein the second arm is associated with the retrieval bag, wherein the first and second arms are configured to open the retrieval bag;

d. an actuating rod in communication with the proximal ends of the first and second arms, wherein the actuating rod is configured to translate longitudinally; and e. a cam actuator associated with the actuating rod, wherein the cam actuator comprises a rotatable body portion configured to rotate to thereby move the first and second arms away from each other to open the retrieval bag.

2. The surgical instrument of claim 1, further comprising an introducer tube, wherein the actuating rod is translatable within the introducer tube.

3. The surgical instrument of claim 2, further comprising a plug, wherein a portion of the plug is disposed within a distal end of the introducer tube, wherein the plug is pivotally attached to the cam actuator and the first and second arms, wherein the plug further comprises a tab projecting transversely from the plug.

4. The surgical instrument of claim 3, wherein the introducer tube comprises a transverse opening near a distal end of the introducer tube, wherein the opening is configured to receive the tab of the plug during deployment of the retrieval bag.

5. The surgical instrument of claim 3, wherein the cam actuator comprises a pair of actuating arms extending from the rotatable body to the actuating rod, wherein at least one actuating arm of the pair of actuating arms is configured to translate longitudinally to rotate the rotatable body of the cam actuator.

6. The surgical instrument of claim 1, wherein the cam actuator comprises an elongated projection extending from the rotatable body, wherein the elongated projection contacts the proximal ends of the first and second arms, wherein the elongated projection rotates in unison with the rotatable body of the cam actuator.

7. A surgical instrument for removal of a specimen from a patient, the surgical instrument comprising:

a. a retrieval bag configured to open and close;

b. a first arm and a second arm, each of the first arm and the second arm comprising a proximal end, wherein each of the first and second arms is associated with the retrieval bag, wherein the first and second arms are configured to open the retrieval bag;

c. an actuating rod in communication with the proximal ends of the first and second arms, wherein the actuating rod is configured to translate longitudinally, wherein the actuating rod defines a longitudinal axis; and d. a cam actuator associated with the actuating rod, wherein the cam actuator comprises a rotatable body portion configured to move the first and second arms away from each other to open the retrieval bag, wherein the rotatable body portion is configured to rotate about an axis that is transverse to the longitudinal axis of the actuating rod.

8. The surgical instrument of claim 7, wherein the first and second arms each have a substantially linear shape.

9. The surgical instrument of claim 7, wherein the first and second arms each comprise a distal end, wherein the distal ends of the first and second arms are separate from each other.

10. The surgical instrument of claim 7, wherein the rotatable body portion is configured to rotate from a first position to a second position, wherein a length of the rotatable body portion is substantially parallel to the longitudinal axis of the actuating rod in response to the rotatable body portion being disposed in the first position, and wherein the length of the rotatable body portion is substantially perpendicular to the longitudinal axis of the actuating rod in response to the rotatable body portion being disposed in the second position.

11. The surgical instrument of claim 7, wherein the retrieval bag is configured to be slidably removed from the first and second arms.

12. The surgical instrument of claim 11, further comprising a closure string associated with the retrieval bag, wherein the closure string is configured to close the retrieval bag.

13. The surgical instrument of claim 7, wherein the cam actuator comprises a pair of actuating arms extending from the rotatable body to the actuating rod, wherein one actuating arm of the pair of actuating arms is configured to translate longitudinally relative to the actuating rod to rotate the rotatable body of the cam actuator, wherein the other actuating arm of the pair of actuating arms is fixed relative to the actuating rod.

14. A surgical instrument for removal of a specimen from a patient, the surgical instrument comprising:

a. a retrieval bag configured to open and close;

b. a first arm comprising a proximal end;

c. a second arm comprising a proximal end, wherein the first and second arms are associated with the retrieval bag;

d. an actuating rod in communication with the proximal ends of the first and second arms, wherein the actuating rod is configured to translate longitudinally; and e. a cam actuator associated with the actuating rod, wherein the cam actuator comprises:

(i). a rotatable cam body configured to move the proximal ends of the first and second arms away from each other, wherein the first and second arms are configured to open the retrieval bag when the proximal ends of the first and second arms are moved away from each other, and (ii) a pair of actuating arms extending from the rotatable cam body to the actuating rod, wherein at least one actuating arm of the pair of actuating arms is configured to translate longitudinally to rotate the rotatable cam body of the cam actuator.

15. The surgical instrument of claim 14, wherein the first and second arms comprise distal ends, wherein the distal ends of the first and second arms are spaced apart in response to the movement of the proximal ends of the first and second arms away from each other.

16. The surgical instrument of claim 14, further comprising a plug, wherein the plug is pivotally attached to the cam actuator and the first and second arms, wherein the plug comprises an upwardly extending post configured to be received in a hole disposed in the rotatable cam body.

17. The surgical instrument of claim 16, wherein the rotatable cam body is configured to pivot about the upwardly extending post of the plug.

18. The surgical instrument of claim 14, further comprising an introducer tube, wherein the actuating rod is translatable within introducer tube, wherein the rotatable cam body is configured to rotate about an axis that is transverse to a longitudinal axis of the introducer tube.

19. The surgical instrument of claim 14, wherein one actuating arm of the pair of actuating arms is configured to translate longitudinally relative to the actuating rod to rotate the rotatable body of the cam actuator, wherein the other actuating arm of the pair of actuating arms is fixed relative to the actuating rod.

20. The surgical instrument of claim 14, wherein the first and second arms are configured to move in unison with the actuating rod.

* * * * *